(12) United States Patent
Stahmann et al.

(10) Patent No.: US 8,483,818 B2
(45) Date of Patent: Jul. 9, 2013

(54) ENHANCEMENTS TO THE DETECTION OF PULMONARY EDEMA WHEN USING TRANSTHORACIC IMPEDANCE

(75) Inventors: Jeffrey E. Stahmann, Ramsey, MN (US); John D. Hatlestad, Maplewood, MN (US); Jesse W. Hartley, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 165 days.

(21) Appl. No.: 13/033,081

(22) Filed: Feb. 23, 2011

(65) Prior Publication Data

US 2011/0144526 A1     Jun. 16, 2011

Related U.S. Application Data

(63) Continuation of application No. 11/126,689, filed on May 11, 2005, now Pat. No. 7,907,997.

(51) Int. Cl.
*A61B 5/05*    (2006.01)
*A61B 5/04*    (2006.01)
*A61N 1/00*    (2006.01)

(52) U.S. Cl.
USPC .............................. 600/547; 600/509; 607/18

(58) Field of Classification Search
USPC ... 600/300, 547, 528, 586, 509–514; 607/4–6
See application file for complete search history.

(56) References Cited

U.S. PATENT DOCUMENTS

| | | | |
|---|---|---|---|
| 3,340,867 A | 9/1967 | Kubicek et al. | |
| 3,608,542 A | 9/1971 | Pacela et al. | |
| 3,871,359 A | 3/1975 | Pacela | |
| 4,003,379 A | 1/1977 | Ellinwood, Jr. | |
| 4,059,169 A | 11/1977 | Hagen | |

(Continued)

FOREIGN PATENT DOCUMENTS

| EP | 348271 | 12/1989 |
|---|---|---|
| EP | 0584388 A1 | 3/1994 |

(Continued)

OTHER PUBLICATIONS

U.S. Appl. No. 09/919,483, Supplemental Notice of Allowability mailed Apr. 14, 2006, 2 pgs.

(Continued)

*Primary Examiner* — Brian Szmal
*Assistant Examiner* — H. Q. Nguyen
(74) *Attorney, Agent, or Firm* — Schwegman, Lundberg & Woessner, P.A.

(57) ABSTRACT

This patent document discusses, among other things, systems, devices, and methods for enhancing detection of pulmonary edema using, in addition to thoracic impedance, one or a combination of: physiologic information about a subject, at least one statistical parameter, a user-programmable detection level, at least one parameter associated with a previous pulmonary edema event, and patient symptom information about the subject. In one example, a (base) thoracic impedance threshold is modified to an adjusted thoracic impedance threshold. The adjusted thoracic impedance threshold provides an increased sensitivity of pulmonary edema detection as compared to the base thoracic impedance threshold. In another example, an alert is provided to a subject, a caregiver, or other user based on a pulmonary edema indication determined by the present systems, devices, and methods. In a further example, a therapy (provided to the subject) is adjusted or initiated in response to the pulmonary edema indication.

14 Claims, 10 Drawing Sheets

U.S. PATENT DOCUMENTS

| | | |
|---|---|---|
| RE30,101 E | 9/1979 | Kubicek et al. |
| 4,271,192 A | 6/1981 | Wurtman et al. |
| 4,308,872 A | 1/1982 | Watson et al. |
| 4,437,469 A | 3/1984 | Djordjevich et al. |
| 4,450,527 A | 5/1984 | Sramek |
| 4,470,987 A | 9/1984 | Wurtman et al. |
| 4,472,420 A | 9/1984 | Toth |
| 4,472,431 A | 9/1984 | Toth |
| 4,559,946 A | 12/1985 | Mower |
| 4,562,843 A | 1/1986 | Djordjevich et al. |
| 4,567,892 A | 2/1986 | Plicchi et al. |
| 4,576,183 A | 3/1986 | Plicchi et al. |
| 4,651,716 A | 3/1987 | Forester et al. |
| 4,686,987 A | 8/1987 | Salo et al. |
| 4,693,253 A | 9/1987 | Adams |
| 4,702,253 A | 10/1987 | Nappholz et al. |
| 4,796,639 A | 1/1989 | Snow et al. |
| 4,860,751 A | 8/1989 | Callaghan |
| 4,880,005 A | 11/1989 | Pless et al. |
| 4,884,576 A | 12/1989 | Alt |
| 4,904,472 A | 2/1990 | Belardinelli et al. |
| 4,919,136 A | 4/1990 | Alt |
| 4,980,379 A | 12/1990 | Belardinelli et al. |
| 4,987,897 A | 1/1991 | Funke |
| 4,993,421 A | 2/1991 | Thornton |
| 5,002,052 A | 3/1991 | Haluska |
| 5,003,976 A | 4/1991 | Alt |
| 5,025,786 A | 6/1991 | Siegel |
| 5,025,791 A | 6/1991 | Niwa |
| 5,031,629 A | 7/1991 | DeMarzo |
| 5,036,849 A | 8/1991 | Hauck et al. |
| 5,040,536 A | 8/1991 | Riff |
| 5,113,869 A | 5/1992 | Nappholz et al. |
| 5,117,825 A | 6/1992 | Grevious |
| 5,178,154 A | 1/1993 | Ackmann et al. |
| 5,179,947 A | 1/1993 | Meyerson et al. |
| 5,199,428 A | 4/1993 | Obel et al. |
| 5,213,098 A | 5/1993 | Bennett et al. |
| 5,215,083 A | 6/1993 | Drane et al. |
| 5,233,985 A | 8/1993 | Hudrlik |
| 5,246,008 A | 9/1993 | Mueller et al. |
| 5,271,395 A | 12/1993 | Wahlstrand et al. |
| 5,273,034 A | 12/1993 | Nilsson |
| 5,282,836 A | 2/1994 | Kreyenhagen et al. |
| 5,282,840 A | 2/1994 | Hudrlik et al. |
| 5,284,136 A | 2/1994 | Hauck et al. |
| 5,284,491 A | 2/1994 | Sutton et al. |
| 5,292,343 A | 3/1994 | Blanchette et al. |
| 5,300,093 A | 4/1994 | Koestner et al. |
| 5,309,917 A | 5/1994 | Wang et al. |
| 5,313,953 A | 5/1994 | Yomtov et al. |
| 5,324,309 A | 6/1994 | Kallok |
| 5,324,315 A | 6/1994 | Grevious |
| 5,344,429 A | 9/1994 | Smits |
| 5,354,317 A | 10/1994 | Alt |
| 5,354,319 A | 10/1994 | Wyborny et al. |
| 5,355,894 A | 10/1994 | Sivard |
| 5,366,485 A | 11/1994 | Kroll et al. |
| 5,370,665 A | 12/1994 | Hudrlik |
| 5,391,190 A | 2/1995 | Pederson et al. |
| 5,404,877 A | 4/1995 | Nolan et al. |
| 5,405,362 A | 4/1995 | Kramer et al. |
| 5,411,031 A | 5/1995 | Yomtov |
| 5,431,682 A | 7/1995 | Hedberg |
| 5,441,525 A | 8/1995 | Shelton et al. |
| 5,443,073 A | 8/1995 | Wang et al. |
| 5,454,377 A | 10/1995 | Dzwonczyk et al. |
| 5,464,434 A | 11/1995 | Alt |
| 5,469,861 A | 11/1995 | Piscopo et al. |
| 5,479,369 A | 12/1995 | Matsumura et al. |
| 5,484,401 A | 1/1996 | Rodriguez et al. |
| 5,501,701 A | 3/1996 | Markowitz et al. |
| 5,505,209 A | 4/1996 | Reining |
| 5,507,785 A | 4/1996 | Deno |
| 5,522,860 A | 6/1996 | Molin et al. |
| 5,526,808 A | 6/1996 | Kaminsky |
| 5,534,018 A | 7/1996 | Wahlstrand et al. |
| 5,535,752 A | 7/1996 | Halperin et al. |
| 5,540,728 A | 7/1996 | Shelton et al. |
| 5,562,711 A | 10/1996 | Yerich et al. |
| 5,562,712 A | 10/1996 | Steinhaus et al. |
| 5,593,431 A | 1/1997 | Sheldon |
| 5,626,623 A | 5/1997 | Kieval et al. |
| 5,642,734 A | 7/1997 | Ruben et al. |
| 5,676,686 A | 10/1997 | Jensen et al. |
| 5,685,316 A | 11/1997 | Schookin et al. |
| 5,706,829 A | 1/1998 | Kadri |
| 5,722,999 A | 3/1998 | Snell |
| 5,725,561 A | 3/1998 | Stroebel et al. |
| 5,725,562 A | 3/1998 | Sheldon |
| 5,732,710 A | 3/1998 | Rabinovich et al. |
| 5,735,284 A | 4/1998 | Tsoglin et al. |
| 5,749,369 A | 5/1998 | Rabinovich et al. |
| 5,749,900 A | 5/1998 | Schroeppel et al. |
| 5,782,774 A | 7/1998 | Shmulewitz |
| 5,782,879 A | 7/1998 | Rosborough et al. |
| 5,782,884 A | 7/1998 | Stotts et al. |
| 5,788,643 A | 8/1998 | Feldman |
| 5,791,349 A | 8/1998 | Shmulewitz |
| 5,800,464 A | 9/1998 | Kieval |
| 5,824,029 A | 10/1998 | Weijand et al. |
| 5,865,760 A | 2/1999 | Lidman et al. |
| 5,874,420 A | 2/1999 | Pelleg |
| 5,876,353 A | 3/1999 | Riff |
| 5,882,352 A | 3/1999 | Duncan et al. |
| 5,904,708 A | 5/1999 | Goedeke |
| 5,913,879 A | 6/1999 | Ferek-Petric et al. |
| 5,919,210 A | 7/1999 | Lurie et al. |
| 5,957,861 A | 9/1999 | Combs et al. |
| 5,957,957 A | 9/1999 | Sheldon |
| 5,974,340 A | 10/1999 | Kadhiresan |
| 5,978,705 A | 11/1999 | KenKnight et al. |
| 6,002,963 A | 12/1999 | Mouchawar et al. |
| 6,015,388 A | 1/2000 | Sackner et al. |
| 6,024,704 A | 2/2000 | Meador et al. |
| 6,026,324 A | 2/2000 | Carlson |
| 6,035,233 A | 3/2000 | Schroeppel et al. |
| 6,044,297 A | 3/2000 | Sheldon et al. |
| 6,047,203 A | 4/2000 | Sackner et al. |
| 6,049,735 A | 4/2000 | Hartley et al. |
| 6,075,015 A | 6/2000 | Sestelo et al. |
| 6,076,015 A | 6/2000 | Hartley et al. |
| 6,078,834 A | 6/2000 | Lurie et al. |
| 6,095,987 A | 8/2000 | Shmulewitz et al. |
| 6,104,949 A | 8/2000 | Pitts et al. |
| 6,135,970 A | 10/2000 | Kadhiresan et al. |
| 6,154,672 A | 11/2000 | Pendekanti et al. |
| 6,161,038 A | 12/2000 | Schookin et al. |
| 6,186,955 B1 | 2/2001 | Baura |
| 6,193,668 B1 | 2/2001 | Chassaing et al. |
| 6,224,907 B1 | 5/2001 | Davar et al. |
| 6,228,033 B1 | 5/2001 | Koobi et al. |
| 6,266,565 B1 | 7/2001 | Er et al. |
| 6,272,377 B1 | 8/2001 | Sweeney et al. |
| 6,275,727 B1 | 8/2001 | Hopper et al. |
| 6,292,689 B1 | 9/2001 | Wallace et al. |
| 6,298,267 B1 | 10/2001 | Rosborough et al. |
| 6,314,322 B1 | 11/2001 | Rosenberg |
| 6,317,631 B1 | 11/2001 | Ben-Haim et al. |
| 6,334,063 B1 | 12/2001 | Charlier et al. |
| 6,336,903 B1 | 1/2002 | Bardy |
| 6,409,675 B1 | 6/2002 | Turcott |
| 6,411,840 B1 | 6/2002 | Bardy |
| 6,411,844 B1 | 6/2002 | Kroll et al. |
| 6,438,408 B1 | 8/2002 | Mulligan et al. |
| 6,473,640 B1 | 10/2002 | Erlebacher |
| 6,478,746 B2 | 11/2002 | Chassaing et al. |
| 6,480,733 B1 | 11/2002 | Turcott |
| 6,511,438 B2 | 1/2003 | Bernstein et al. |
| 6,512,949 B1 | 1/2003 | Combs et al. |
| 6,517,481 B2 | 2/2003 | Hoek et al. |
| 6,520,924 B2 | 2/2003 | Lee |
| 6,527,729 B1 | 3/2003 | Turcott |
| 6,560,481 B1 | 5/2003 | Heethaar et al. |
| 6,561,986 B2 | 5/2003 | Baura et al. |
| 6,574,506 B2 | 6/2003 | Kramer et al. |
| 6,575,916 B2 | 6/2003 | Halleck et al. |

| | | |
|---|---|---|
| 6,591,122 B2 | 7/2003 | Schmitt |
| 6,595,927 B2 | 7/2003 | Pitts-Crick et al. |
| 6,600,949 B1 | 7/2003 | Turcott |
| 6,602,201 B1 | 8/2003 | Hepp |
| 6,625,492 B1 | 9/2003 | Florio et al. |
| 6,626,821 B1* | 9/2003 | Kung et al. ............... 600/16 |
| 6,636,754 B1 | 10/2003 | Baura et al. |
| 6,643,543 B2 | 11/2003 | Takehara et al. |
| 6,647,295 B2 | 11/2003 | Florio et al. |
| 6,658,292 B2 | 12/2003 | Kroll et al. |
| 6,662,047 B2 | 12/2003 | Sorensen et al. |
| 6,665,564 B2 | 12/2003 | Lincoln et al. |
| 6,678,547 B2 | 1/2004 | Carlson et al. |
| 6,692,446 B2 | 2/2004 | Hoek |
| 6,714,813 B2 | 3/2004 | Ishigooka et al. |
| 6,738,671 B2 | 5/2004 | Christophersom et al. |
| 6,748,271 B2 | 6/2004 | Hoek et al. |
| 6,752,765 B1 | 6/2004 | Jensen et al. |
| 6,811,537 B2 | 11/2004 | Bardy |
| 6,829,503 B2 | 12/2004 | Alt |
| 6,907,288 B2 | 6/2005 | Daum |
| 6,908,437 B2 | 6/2005 | Bardy |
| 6,912,420 B2 | 6/2005 | Scheiner et al. |
| 6,978,182 B2 | 12/2005 | Mazar et al. |
| 7,003,346 B2 | 2/2006 | Singer |
| 7,149,573 B2 | 12/2006 | Wang |
| 7,177,681 B2 | 2/2007 | Zhu et al. |
| 7,191,000 B2 | 3/2007 | Zhu et al. |
| 7,226,422 B2 | 6/2007 | Hatlestad et al. |
| 7,333,854 B1 | 2/2008 | Brewer et al. |
| 7,340,296 B2 | 3/2008 | Stahmann et al. |
| 7,384,395 B2 | 6/2008 | Hatlestad et al. |
| 7,387,610 B2 | 6/2008 | Stahmann et al. |
| 7,422,560 B2 | 9/2008 | Hatlestad et al. |
| 7,480,528 B2 | 1/2009 | Brockway et al. |
| 7,662,101 B2 | 2/2010 | Lee et al. |
| 7,672,718 B2 | 3/2010 | Stahmann et al. |
| 7,819,804 B2 | 10/2010 | Hatlestad et al. |
| 7,881,781 B2 | 2/2011 | Stahmann et al. |
| 7,907,997 B2 | 3/2011 | Stahmann et al. |
| 2001/0020138 A1 | 9/2001 | Ishigooka et al. |
| 2002/0004670 A1 | 1/2002 | Florio et al. |
| 2002/0032386 A1 | 3/2002 | Sackner et al. |
| 2002/0091326 A1 | 7/2002 | Hashimoto et al. |
| 2002/0115939 A1 | 8/2002 | Mulligan et al. |
| 2002/0123674 A1 | 9/2002 | Plicchi et al. |
| 2002/0128563 A1 | 9/2002 | Carlson et al. |
| 2002/0138014 A1 | 9/2002 | Baura et al. |
| 2002/0147475 A1 | 10/2002 | Scheiner et al. |
| 2002/0147476 A1 | 10/2002 | Daum |
| 2002/0161287 A1* | 10/2002 | Schmitt ............... 600/310 |
| 2002/0169484 A1* | 11/2002 | Mathis et al. ............... 607/9 |
| 2002/0170193 A1 | 11/2002 | Townsend et al. |
| 2002/0193689 A1 | 12/2002 | Bernstein et al. |
| 2003/0023279 A1 | 1/2003 | Spinelli et al. |
| 2003/0028221 A1 | 2/2003 | Zhu et al. |
| 2003/0055461 A1 | 3/2003 | Girouard et al. |
| 2003/0074029 A1 | 4/2003 | Deno et al. |
| 2003/0105496 A1 | 6/2003 | Yu et al. |
| 2003/0139679 A1 | 7/2003 | Kushnir et al. |
| 2003/0176896 A1 | 9/2003 | Lincoln et al. |
| 2003/0191503 A1 | 10/2003 | Zhu et al. |
| 2003/0220580 A1 | 11/2003 | Alt |
| 2004/0039295 A1 | 2/2004 | Olbrich et al. |
| 2004/0049235 A1 | 3/2004 | Deno et al. |
| 2004/0073093 A1 | 4/2004 | Hatlestad |
| 2004/0073128 A1 | 4/2004 | Hatlestad et al. |
| 2004/0073262 A1 | 4/2004 | Lovett |
| 2004/0086864 A1 | 5/2004 | Lo et al. |
| 2004/0102712 A1 | 5/2004 | Belalcazar et al. |
| 2004/0116819 A1 | 6/2004 | Alt |
| 2004/0127807 A1 | 7/2004 | Hatlesad et al. |
| 2004/0133079 A1 | 7/2004 | Mazar et al. |
| 2004/0147982 A1 | 7/2004 | Bardy |
| 2004/0172080 A1 | 9/2004 | Stadler et al. |
| 2004/0186523 A1 | 9/2004 | Florio |
| 2004/0215097 A1 | 10/2004 | Wang |
| 2004/0215270 A1 | 10/2004 | Ritscher et al. |
| 2005/0004609 A1 | 1/2005 | Stahmann et al. |
| 2005/0021098 A1 | 1/2005 | Spinelli et al. |
| 2005/0043675 A1 | 2/2005 | Pastore et al. |
| 2005/0065448 A1 | 3/2005 | Stahmann et al. |
| 2005/0080460 A1 | 4/2005 | Wang et al. |
| 2005/0119586 A1 | 6/2005 | Coyle et al. |
| 2005/0124908 A1 | 6/2005 | Belalcazar et al. |
| 2005/0137480 A1 | 6/2005 | Alt et al. |
| 2005/0145246 A1 | 7/2005 | Hartley et al. |
| 2005/0177062 A1 | 8/2005 | Skrabal et al. |
| 2005/0283197 A1 | 12/2005 | Daum et al. |
| 2005/0288721 A1 | 12/2005 | Girouard et al. |
| 2006/0020295 A1 | 1/2006 | Brockway et al. |
| 2006/0041280 A1 | 2/2006 | Stahmann et al. |
| 2006/0134071 A1 | 6/2006 | Ross et al. |
| 2006/0134079 A1 | 6/2006 | Sih et al. |
| 2006/0135886 A1 | 6/2006 | Lippert et al. |
| 2006/0224201 A1 | 10/2006 | Hettrick et al. |
| 2006/0241512 A1 | 10/2006 | Kwok et al. |
| 2006/0258952 A1 | 11/2006 | Stahmann et al. |
| 2006/0264776 A1 | 11/2006 | Stahmann et al. |
| 2006/0293609 A1 | 12/2006 | Stahmann et al. |
| 2007/0054871 A1 | 3/2007 | Pastore et al. |
| 2007/0106130 A1 | 5/2007 | Hatlestad et al. |
| 2007/0118054 A1 | 5/2007 | Pinhas et al. |
| 2007/0129641 A1 | 6/2007 | Sweeney |
| 2007/0129643 A1 | 6/2007 | Kwok et al. |
| 2008/0045852 A1 | 2/2008 | Hatlestad et al. |
| 2008/0108907 A1 | 5/2008 | Stahmann et al. |
| 2008/0146928 A1* | 6/2008 | Dala-Krishna ............... 600/443 |
| 2008/0249433 A1 | 10/2008 | Stahmann et al. |
| 2009/0005697 A1 | 1/2009 | Hatlestad et al. |
| 2009/0132000 A1 | 5/2009 | Brockway et al. |
| 2010/0076336 A1 | 3/2010 | Stahmann |
| 2011/0009709 A1 | 1/2011 | Hatlestad et al. |

FOREIGN PATENT DOCUMENTS

| | | |
|---|---|---|
| EP | 0620420 | 10/1994 |
| EP | 0663219 A1 | 7/1995 |
| EP | 0985429 A2 | 3/2000 |
| EP | 1057498 | 12/2000 |
| EP | 1078597 | 2/2001 |
| EP | 1151719 A2 | 11/2001 |
| EP | 606301 | 12/2001 |
| EP | 1247487 | 10/2002 |
| EP | 1275342 | 1/2003 |
| EP | 771172 | 4/2003 |
| JP | 03109277 U | 11/1991 |
| JP | 05048904 A2 | 2/1993 |
| JP | 05048904 | 6/1993 |
| JP | 06-327653 A | 11/1994 |
| JP | 2003-088512 | 3/2003 |
| JP | 2003-088512 A | 3/2003 |
| JP | 2006327653 A2 | 12/2006 |
| WO | WO-8400227 | 1/1984 |
| WO | WO-9304627 | 3/1993 |
| WO | WO-9601586 | 1/1996 |
| WO | WO-9737591 | 10/1997 |
| WO | WO-9738628 | 10/1997 |
| WO | WO-9851211 | 11/1998 |
| WO | WO-0119426 A2 | 3/2001 |
| WO | WO-0141638 | 6/2001 |
| WO | WO-0178577 A2 | 10/2001 |
| WO | WO-02/40096 A1 | 5/2002 |
| WO | WO-02053026 | 7/2002 |
| WO | WO-02053228 | 7/2002 |
| WO | WO-03020364 | 3/2003 |
| WO | WO-2004012815 A1 | 2/2004 |
| WO | WO-2004050178 A1 | 6/2004 |
| WO | WO-2006028575 A2 | 3/2006 |
| WO | WO-2006028575 A3 | 3/2006 |

OTHER PUBLICATIONS

U.S. Appl. No. 09/919,483, Non-Final Office Action mailed Aug. 22, 2002, 5 pgs.

U.S. Appl. No. 09/919,483, Non-Final Office Action mailed Sep. 22, 2003, 6 pgs.

U.S. Appl. No. 09/919,483, Non-Final Office Action mailed Oct. 4, 2004, 8 pgs.

U.S. Appl. No. 09/919,483, Notice of Allowance mailed Feb. 6, 2003, 6 pgs.
U.S. Appl. No. 09/919,483, Notice of Allowance mailed Feb. 24, 2006, 7 pgs.
U.S. Appl. No. 09/919,483, Notice of Allowance mailed Mar. 22, 2005, 6 pgs.
U.S. Appl. No. 09/919,483, Notice of Allowance mailed Sep. 21, 2006, 5 pgs.
U.S. Appl. No. 09/919,483, Response filed Nov. 22, 2002 to Non-Final Office Action mailed Aug. 22, 2002, 8 pgs.
U.S. Appl. No. 09/919,483, Response filed Dec. 22, 2003 to Non-Final Office Action mailed Sep. 22, 2003, 12 pgs.
U.S. Appl. No. 09/919,483, Response filed Dec. 30, 2004 to Non-Final Office Action mailed Oct. 4, 2004, 13 pgs.
U.S. Appl. No. 10/267,982, Amendment and Response filed Oct. 3, 2005 to Non-Final Office Action mailed May 2, 2005, 15 pgs.
U.S. Appl. No. 10/267,982, Non-Final Office Action mailed May 2, 2005, 7 pgs.
"U.S. Appl. No. 10/267,982, Amendment and Response filed Oct. 3, 2005 to Non-Final Office Action mailed May 2, 2005", 15 pgs.
"U.S. Appl. No. 10/267,982, Non-Final Office Action mailed May 2, 2005", 7 pgs.
"U.S. Appl. No. 10/267,982, Notice of Allowance mailed Jun. 2, 2006", 7 pgs.
"U.S. Appl. No. 10/267,982, Notice of Allowance mailed Oct. 3, 2006", 7 pgs.
"U.S. Appl. No. 10/267,982, Notice of Allowance mailed Dec. 29, 2005", 6 pgs.
"U.S. Appl. No. 10/267,982, Supplemental Amendment filed Jan. 18, 2006", 12 pgs.
"U.S. Appl. No. 10/267,982, Supplemental Amendment filed Aug. 29, 2006", 13 pgs.
"U.S. Appl. No. 10/411,795, Non-Final Office Action mailed Apr. 14, 2006", 13 pgs.
"U.S. Appl. No. 10/411,795, Non-Final Office Action mailed Nov. 1, 2005", 12 pgs.
"U.S. Appl. No. 10/411,795, Notice of Allowance mailed Sep. 29, 2006", 5 pgs.
"U.S. Appl. No. 10/411,795, Response filed Jan. 13, 2006 to Non-Final Office Action mailed Nov. 1, 2005", 22 pgs.
"U.S. Appl. No. 10/411,795, Response filed Jul. 11, 2006 to Non-Final Office Action mailed Apr. 14, 2006", 22 pgs.
"U.S. Appl. No. 10/921,503, Amendment and Response filed Oct. 12, 2007 to Non-Final Office Action mailed Jul. 13, 2007", 21 pgs.
"U.S. Appl. No. 10/921,503, Notice of Allowance mailed Jan. 31, 2008", 8 pgs.
"U.S. Appl. No. 10/921,503, Response filed Apr. 9, 2007 to Restriction Requirement mailed Mar. 7, 2007", 19 pgs.
"U.S. Appl. No. 10/921,503, Restriction Requirement mailed Mar. 7, 2007", 6 pgs.
"U.S. Appl. No. 10/921,503, Supplemental Amendment and Response filed Oct. 25, 2007 to Office Action mailed Jul. 13, 2007", 24 pgs.
"U.S. Appl. No. 10/921,503, Non-Final Office Action mailed Jul. 13, 2007", 5 pgs.
"U.S. Appl. No. 11/126,689, Advisory Action mailed Aug. 27, 2007", 3 pgs.
"U.S. Appl. No. 11/126,689, Appeal Brief filed Aug. 31, 2010", 31 pgs.
"U.S. Appl. No. 11/126,689, Final Office Action mailed Mar. 12, 2010", 16 pgs.
"U.S. Appl. No. 11/126,689, Final Office Action mailed Jan. 14, 2007", 13 pgs.
"U.S. Appl. No. 11/126,689, Non-Final Office Action mailed Jan. 3, 2007", 9 pgs.
"U.S. Appl. No. 11/126,689, Non-Final Office Action mailed Feb. 6, 2009", 14 pgs.
"U.S. Appl. No. 11/126,689, Non-Final Office Action mailed Jul. 21, 2008", 6 pgs.
"U.S. Appl. No. 11/126,689, Non-Final Office Action mailed Oct. 19, 2007", 11 pgs.
"U.S. Appl. No. 11/126,689, Notice of Allowance mailed Nov. 10, 2010", 10 pgs.
"U.S. Appl. No. 11/126,689, Response filed Oct. 10, 2006 to Restriction Requirement mailed Sep. 8, 2006", 12 pgs.
"U.S. Appl. No. 11/126,689, Response filed Jan. 22, 2008 to Non-Final Office Action mailed Oct. 19, 2007", 23 pgs.
"U.S. Appl. No. 11/126,689, Response filed Apr. 3, 2007 to Non-Final Office Action mailed Jan. 3, 2007", 22 pgs.
"U.S. Appl. No. 11/126,689, Response filed Aug. 14, 2007 to Final Office Action mailed Jun. 14, 2007", 13 pgs.
"U.S. Appl. No. 11/126,689, Response filed Oct. 19, 2009 to Restriction Requirement mailed Sep. 17, 2009", 16 pgs.
"U.S. Appl. No. 11/126,689, Response filed Oct. 21, 2008 to Non Final Office Action mailed Jul. 21, 2008", 13 pgs.
"U.S. Appl. No. 11/126,689, Response filed Jun. 10, 2009 to Non Final Office Action mailed Feb. 6, 2009", 18 pgs.
"U.S. Appl. No. 11/126,689, Restriction Requirement mailed Sep. 8, 2006", 5 pgs.
"U.S. Appl. No. 11/126,689, Restriction Requirement mailed Sep. 17, 2009", 6 pgs.
"U.S. Appl. No. 11/126,723, Non-Final Office Action Mailed Oct. 30, 2007", 7 pgs.
"U.S. Appl. No. 11/126,723, Restriction Requirement mailed Sep. 6, 2007", 5 pgs.
"U.S. Appl. No. 11/126,723, Response filed Jan. 12, 2009 to Final Office Action mailed Aug. 11, 2008", 20 pgs.
"U.S. Appl. No. 11/126,723, Response filed Jan. 30, 2008 to Non-Final Office Action mailed Oct. 30, 2007", 20 pgs.
"U.S. Appl. No. 11/126,723, Response filed Oct. 14, 2008 to Final Office Action mailed Aug. 11, 2008", 18 pgs.
"U.S. Appl. No. 11/126,723, Response filed Oct. 9, 2007 to Restriction Requirement mailed Sep. 6, 2007", 14 pgs.
"U.S. Appl. No. 11/126,723, Advisory Action mailed Nov. 13, 2008", 3 pgs.
"U.S. Appl. No. 11/126,723, Non-Final Office Action mailed Apr. 29, 2009", 9 pgs.
"U.S. Appl. No. 11/126,723, Final Office Action mailed May 13, 2010", 9 pgs.
"U.S. Appl. No. 11/126,723, Response filed Aug. 31, 2009 to Non-Final Office Action mailed Apr. 29, 2009", 20 pgs.
"U.S. Appl. No. 11/126,723, Response filed Sep. 1, 2010 to Final Office Action mailed May 13, 2010", 19 pgs.
"U.S. Appl. No. 11/619,821, Notice of Allowance Mailed Aug. 24, 2007", 7 pgs.
"U.S. Appl. No. 11/619,821, Response filed Jul. 16, 2007 to Restriction Requirement mailed Jun. 14, 2007", 8 pgs.
"U.S. Appl. No. 11/619,821, Restriction Requirement mailed Jun. 14, 2007", 5 pgs.
"U.S. Appl. No. 11/926,425, Notice of Allowance mailed Apr. 1, 2008", 6 pgs.
"U.S. Appl. No. 11/926,425, Amendment filed Jul. 1, 2008 in Response to Notice of Allowance mailed Apr. 1, 2008", 4 pgs.
"U.S. Appl. No. 11/926,425, Preliminary Amendment mailed Nov. 21, 2007", 7 pgs.
"U.S. Appl. No. 11/926,425, Response to Rule 312 Communication mailed Aug. 8, 2008", 2 pgs.
"U.S. Appl. No. 12/139,948, Non-Final Office Action mailed Feb. 6, 2009", 6 pgs.
"U.S. Appl. No. 12/139,948, Notice of Allowance mailed Sep. 4, 2009", 6 pgs.
"U.S. Appl. No. 12/139,948, Response filed Apr. 27, 2009 to Non Final Office Action mailed Feb. 6, 2009", 8 pgs.
"U.S. Appl. No. 12/204,152, Non-Final Office Action mailed Mar. 19, 2010", 5 pgs.
"U.S. Appl. No. 12/204,152, Notice of Allowance mailed Jun. 23, 2010", 4 Pgs.
"U.S. Appl. No. 12/204,152, Response filed May 24, 2010 to Non-Final Office Action mailed Mar. 19, 2010", 7 pgs.
"U.S. Appl. No. 12/628,384, Non-Final Office Action mailed Apr. 6, 2010", 5 pgs.
"U.S. Appl. No. 12/628,384, Notice of Allowance mailed Sep. 28, 2010", 7 pgs.
"U.S. Appl. No. 12/628,384, Response filed Jul. 9, 2010 to Non-Final Office Action mailed Apr. 6, 2010", 12 pgs.

"U.S. Appl. No. 11/126,723, Final Office Action Mailed Aug. 11, 2008", 9 pgs.

"European Application Serial No. 03786528.4, Communication mailed Aug. 17, 2009", 4 pgs.

"European Application Serial No. 03786528.4, Response filed Jan. 29, 2010 to Communication mailed Aug. 17, 2009", 19 pgs.

"Heart Sounds", [online]. [retrieved on Dec. 8, 2005]. Retrieved from the Internet: <URL: http://www.chfpatients.com/faq/s3s4.htm>, 4 pgs.

"International Application No. PCT/US2003/032553, International Search Report mailed Jun. 17, 2004", 4 pgs.

"Japanese Application Serial No. 2005-510603, Amendment filed Mar. 30, 2010 in Response to Office Action mailed Dec. 2, 2009", (w/ English Translation of Amended Claims), 37 pgs.

"Japanese Application Serial No. 2005-510603, Notice of Allowance mailed Apr. 20, 2010", 3 pgs.

"Japanese Application Serial No. 2005-510603, Office Action mailed Dec. 2, 2009", (w/ English Translation), 6 pgs.

"Medtronic Announces European Release of Innovative InSync Sentry Cardiac Resynchronization Therapy Defibrillator", http://www.medtronic.com/newsroom/news_20040614a.html, (2004).

Adamicza, A., et al., "Changes in transthoracic electrical impedance during endotoxemia in dogs", Acta Physiol Hung., 85(4), (1997-98), 291-302.

Adamicza, A., et al., "Investigation of the thoracic electrical impedance during endotoxemia in dogs", Acta Chir Hung., 36(1-4), (1997), 1-3.

Alt, Eckhard, et al., "Control of Pacemaker Rate by Impedance-based Respiratory Minute Ventilation*", Chest, 92(2), (Aug. 1987), 247-252.

Baarends, E. M., et al., "Body-water compartments measured by bio-electrical impedance spectroscopy in patients with chronic obstructive pulmonary disease", Clinical Nutrition, 17(1), (Feb. 1998), 15-22.

Belalcazar, Andres, et al., "Improved lung edema monitoring with coronary vein pacing leads", Pacing and Clinical Electrophysiology, 26(4 pt. II), Abstract 18, (Apr. 2003), 933.

Belalcazar, Andres, et al., "Improved lung edema monitoring with coronary vein pacing leads: a simulation study", Physiological Measurement, vol. 25, (2004), 475-487.

Berman, Irwin R, et al., "Transthoracic electrical impedance s a guide to intravascular overload", Archives of Surgery, 102(1), (Jan. 1971), 61-64.

Bradbury, M. G., et al., "Assessment of the sensitivity of bioimpedance to volume changes in body water", Pediatr Nephrol., 9(3), (Jun. 1995), 337-40.

Bussmann, W. D., et al., "Effect of Nitroglycerin Sublingualiy in the Emergency Management of "Classical" Pulmonary Oedema.", Deutsche medizinische Wochenschrift, 102(10), (1946), 9 pgs.

Campbell, J. H, et al., "Clinical applications of electrical impedance tomography in the monitoring of changes in intrathoracic fluid volumes", Physiol. Meas., vol. 15, (1994), A217-A222.

Campbell, J. H., et al., "Detection of changes in intrathoracic fluid in man using electrical impedance tomography", Clinical Science, vol. 87, (1994), 97-101.

Charach, Gideon, et al., "Transthoracic monitoring of the impedance of the right lung in patients with cardiogenic pulmonary edema", Critical Care Medicine, 29(6), (Jun. 2001), 1137-44.

Chiolero, R. L., et al., "Assessment of changes in body water by bioimpedance in acutely ill surgical patients.", Intensive Care Medicine, 18(6), (1992), 322-6.

Defaye, P., et al., "Automatic Recognition of Abnormal Respiratory Events During Sleep by a Pacemaker Transthoracic Impedance Sensor", Journal of Cardiovascular Electrophysiology, 15(9), (Sep. 2004), 1034-40.

Denniston, J. C, et al., "Factors Influencing the measurement of stroke volume by electrical impedance", Physiology (1372-1377), Abstract No. 1373, 463.

Denniston, J. C., et al., "Measurement of pleural effusion by electrical impedance.", Journal of Applied Physiology, 38(5), (May 1975), 851-7.

Ebert, T J, et al., "The use of thoracic impedance for determining thoracic blood volume changes in man", Aviat Space Environ Med., 57(1), (Jan. 1986), 49-53.

Ellenbogen, Kenneth A, et al., "Rate-adaptive pacing based on impedance-derived minute ventilation", Clinical Cardiac Pacing, Philadelphia : Saunders, (1995), 219-233.

Ellenbogen, Kenneth A, et al., "The Electrode-Tissue Interface and the Foreign Body Response", Clinical Cardiac Pacing, Philadelphia : Saunders, (1995), 22-23.

Fein, Alan, et al., "Evaluation of Transthoracic Electrical Impedance in the Diagnosis of Pulmonary Edema", Circulation, 60(5), (Nov. 1979), 1156-1160.

Fleischhauer, J., et al., "Electrical resistances of interstitial and microvascular space as determinants of the extracellular electrical field and velocity of propagation in ventricular myocardium", Circulation, 92(3), (Aug. 1, 1995), 587-594.

Foreman, B, et al., "Intra-thoracic impedance: a surrogate measure of thoracic fluid—fluid accumulation status trial (FAST)", Journal of Cardiac Failure, 10(4 Suppl), Abstract 251, (2004), S86.

Forro, M., et al., "Total body water and ECFV measured using bioelectrical impedance analysis and indicator dilution in horses", Journal of Applied Physiology, 89(2), (Aug. 2000), 663-71.

Frerichs, I., et al., "Electrical impedance tomography in monitoring experimental lung injury", Intensive Care Med., 24(8), (Aug. 1998), 829-36.

Garland, J. S., et al., "Measurement of extravascular lung water in hemodialysis patients using blood ultrasound velocity and optical density dilution.", ASAIO Journal 2002 48(4), (Jul.-Aug. 2002), 398-403.

Goovaerts, H. G, et al., "Microprocessor-based system for measurement of electrical impedances during haemodialysis and in postoperative care", Medical & Biological Engineering & Computing, vol. 26, (Jan. 1988), 75-80.

Gotshall, R W, et al., "Bioelectric impedance as an index of thoracic fluid.", Aviation Space and Environmental Medicine, 70(1), (Jan. 1999), 58-61.

Grimbert, F., et al., "Pulmonary water and thoracic impedance. Evaluation of a measurement technic]", Annales de L'anesthésiologie Française, 16 Spec No. 2-3, French, (1975), 157-63.

Handa, T, "Orthopnea and Respiratory Distress", Clinician, 22(10), (Oct. 10, 1996), 2243-2246.

Harris, N. D., et al., "Applications of applied potential tomography (APT) in respiratory medicine", Clinical Physics and Physiological Measurement, 8 Suppl A, (1987), 155-65.

Hatlestad, J. D, et al., "Physiological Response to Posture Change", U.S. Appl. No. 11/466,925, filed Aug. 24, 2006, 21 pgs.

Hoon, Raghunath Singh, et al., "Changes in Transthoracic electrical impedance at high altitude", British Heart Journal, vol. 39, (1977), 61-66.

Hull, E. T, et al., "The Transthoracic Impedance Method for the Determination of the Degree and Change in Extravascular Water", Acta Tuberc. Pneumol. Belg., 68(4), (1977), 369-377.

Hull, E. T, et al., "Transthoracic electrical impedance: artifacts associated with electrode movement", Resuscitation, 6(2), (1978), 115-124.

Ishibe, Y., et al., "Transthoracic electrical impedance method for measurement of pulmonary edema in vivo", Masui; 27(13), Japanese, (Dec. 1978), 1559-67.

Joekes, A. M, et al., "Impedance Cardiography—Its value in an intensive care unit", D) Materiels et techniques/Cardiocirculatory Equipment and Technics, Abstract No. 141, 1 Page.

Keller, Guido, et al., "Monitoring of Pulmonary Fluid Volume and Stroke Volume by Impedance Cardiography in Patients on Hemodialysis", Chest, 72(1), (Jul. 1977), 56-62.

Khan, Mahfooz R, et al., "Quantitative electrical-impedance plethysmography for pulmonary oedema", Medical & Biological Engineering & Computing, vol. 15, (Nov. 1977), 627-633.

Kiesler, T. W., et al., "Impedance cardiography by use of a spot-electrode array to track changes in cardiac output in anesthetized dogs.", Journal of the American Veterinary Medical Association, 196(11), (Jun. 1, 1990), 1804-10.

Koizumi, T., "Changes of transthoracic impedance (zinf0 and deltaz) in newborn infants", Acta Neonatol. Jpn., 14(3), (1978), 335-340.

Kunst, P. W., et al., "Electrical impedance tomography in the assessment of extravascular lung water in noncardiogenic acute respiratory failure", Chest, 116(6), (Dec. 1999), 1695-702.

Kurimoto, et al., "A Case of Pulmonary Edema in a Horse Treated for Cardiac Ailments", J. Equine Sci, vol. 13 No. 1., (2002), 29-34.

Kusumoto, Fred M, et al., "Medical Progress: Cardiac Pacing", New England Journal of Medicine, 334(2), (Jan. 11, 1996), 89-98.

Larsen, F., et al., "Influence of furosemide and body posture on transthoracic electrical impedance in AMI", Chest, 90(5), (733-7), Nov. 1986.

Laszlo, Z., et al., "Cardiovascular and Hormonal Changes with Different Angles of Head-up Tilt in Men", Physiol. Res., vol. 50, (2001), 71-82.

Lau, C P, et al., "Rate-responsive pacing with a pacemaker that detects respiratory rate (Biorate): clinical advantages and complications", Clinical Cardiology, 11(5), (May 1988), 318-24.

Lau, C. P., "The range of sensors and algorithms used in rate adaptive cardiac pacing", Pacing and clinical electrophysiology: PACE, 15(8), (Aug. 1992), 1177-211.

Leung, Zoe KC, et al., "Feasibility of an automatic atrial and ventricular threshold determination using thransthoracic using impedance", Pacing and Clinical Electrophysiology, vol. 19, Part II, Abstract 263, (Apr. 1996), 631.

Lucas, C., "Congestive Heart Failure, Freedom from Congestion Predicts Good Survival Despite Previous Class IV Symptoms of Heart Failure", American Heart Journal, 140(6), (Dec. 2000), 840-847.

Luepker, R. V., et al., "Transthoracic Electrical Impedance: Quantitative Evaluation of a Non-Invasive Measure of Thoracic Fluid Volume", American Heart Journal, 85(1), (Jan. 1973), 83-93.

Mai, J., et al., "Enhanced Rate Response Algorithm for Orthostatic Compensation Pacing", Pacing Clin Electrophysiol, 23, Naspe Abstracts, Abstract No. 678, (Apr. 2000), 722.

McCarty, Richard N, et al., "Assessment of pulmonary edema in acute congestive heart failure with impedance cardiography", J Am Osteopath Assoc., 74(9), (May 1975), 879.

McNamee, James E, et al., "Peribronchial electrical admittance measures lung edema and congestion in the dog", Special Communications, Electrical Admittance and Pulmonary Edema, 337-341.

Newell, J. C., et al., "Assessment of acute pulmonary edema in dogs by electrical impedance imaging", IEEE Transactions on Biomedical Engineering, 43(2), (Feb. 1996), 133-138.

Nierman, D. M., et al., "Evaluation of transthoracic bioelectrical impedance analysis in monitoring lung water during diuresis", Applied Cardiopulmonary Pathophysiology, 7(1), (1997), 57-62.

Nierman, David M, "Transthoracic Bioimpedance Can Measure Extravascular Lung Water in Acute Lung Injury1", Journal of Surgical Research 65, Article No. 0350, (1996), 101-108.

Noble, T. J., et al., "Diuretic induced change in lung water assessed by electrical impedance tomography", Physiol Meas., 21(1), (Feb. 2000), 155-63.

Nukiwa, Toshihiro, et al., "Responses of Serum and Lung Angiotensin-Converting Enzyme Activities in the Early Phase of Pulmonary Damage Induced by Oleic Acid in Dogs", Am Rev Respir Dis., 126(6), (Dec. 1982), 1080-1086.

Petersen, J. R., et al., "Electrical impedance measured changes in thoracic fluid content during thoracentesis", Clin Physiol., 14(4), (Jul. 1994), 459-66.

Petersen, M E, et al., "Cardiac pacing for vasovagal syncope: a reasonable therapeutic option?", Pacing Clin Electrophysiol., 20(3 Pt 2), (Mar. 1997), 824-6.

Platia, Edward V, et al., "Time Course of Transvenous Pacemaker Stimulation Impedance, Capture Threshold, and Electrogram Amplitude", Pacing Clin Electrophysiol., 9(5), (Sep./Oct. 19), 620-625.

Pomerantz, M, et al., "Transthoracic electrical impedance for the early detection of pulmonary edema", Surgery, 66(1), (Jul. 1969), 260-8.

Raaijmakers, E., et al., "Estimation of non-cardiogenic pulmonary oedema using dual-frequency electrical impedance.", Medical & Biological Engineering & Computing, 36(4), (Jul. 1998), 461-6.

Raggueneau, J. L, et al., "Monitoring of intracellular and extracellular hydric compartments by body impedance", Anesth Anal. Rean, vol. 36, (1979), 439-443.

Ramos, Marcos U, et al., "Transthoracic electric impedance. A clinical guide of pulmonary fluid accumulation in congestive heart failure", Minnesota Medicine, 58(9), (Sep. 1975), 671-676.

Rosborough, John P, et al., "Electrical Therapy for Pulseless Electrical Activity", NASPE, 23(4), Part II, Abstract, (Apr. 2000), 591.

Saunders, Charles E, "The Use of Transthoracic Electrical Bioimpedance in Assessing Thoracic Fluid Status in Emergency Department Patients", American Journal of Emergency Medicine, 6(4), (Jul. 1988), 337-340.

Schuster, C. J, et al., "Application of Impedance Cardiography in Critical Care Medicine", Resuscitation, vol. 11, (1984), 255-274.

Schwartzman, David, et al., "Serial Defibrillation Lead Impedance in Patients with Epicardial and Nonthoracotomy Lead Systems", Journal of Cardiovascular Electrophysiology, 7(8), (Aug. 1996), 697-703.

Segev, G., et al., "B-Type Natriuretic Peptide: A Novel Clinical Tool for Diagnosis and Management of Heart Failure", Hospital Physician, ., (Sep. 2003), 19-24.

Shochat, M., et al., "Internal thoracic impedance monitoring: a new prospect in acute heart failure", European Heart Journal, 25(Supp), (Aug.-Sep. 2004), P72-72.

Shoemaker, William C, et al., "Multicenter trial of a new thoracic electrical bioimpedance device for cardiac output estimation", Critical Care Medicine, 22(12), (Dec. 1994), 1907-1912.

Smith, R. M., et al., "Canine thoracic electrical impedance with changes in pulmonary gas and blood volumes.", Journal of Applied Physiology, 53(6), (Dec. 1982), 1608-13.

Spinale, F. G., et al., "Noninvasive estimation of extravascular lung water using bioimpedance.", The Journal of Surgical Research, 47(6), (Dec. 1989), 535-40.

Sra, J S, et al., "Cardiac pacing during neurocardiogenic (vasovagal) syncope", J Cardiovasc Electrophysiol., 6(9), (Sep. 1995), 751-60.

Stadler, R., et al., "Automated detection of decreases in intrathoracic impedance to predict CHF hospitalization", Abstract 263, 26(4 pt II), Abstract 16, (Apr. 2003), 932.

Stahmann, Jeffrey E, et al., "Improved Sensitivity and Specificity of Pulmonary Edema Detection When Using Transthoracic Impedance", U.S. Appl. No. 11/126,723, filed May 11, 2005, 64 pgs.

Staub, N. C., "The measurement of lung water content.", The Journal of Microwave Power, 18(3), (Sep. 1983), 259-63.

Tang, W., "Assessment of total body water using bioelectrical impedance analysis in neonates receiving intensive care", Arch Dis Child Fetal Neonatal Ed., 77(2), (Sep. 1997), F123-6.

Tempel, G., et al., "Transthoracic electrical impendance in anaesthesia and intensive care.", Resuscitation, 6(2), (1978), 97-105.

Thakur, Ranjan K, et al., "Pericardial Effusion Increases Defibrillation Energy Requirement", Pacing Clin Electrophysiol., 16(6), (Jun. 1993), 1227-1230.

Vainshtein, G. B, et al., "The Functioning of the Cerebral Circulation System in Hyperthermia in Rabbits", Fiziol Zh SSSR Im I M Sechenova, 75(11), (Nov. 1989), 1608-1614.

Van De Water, Joseph M, et al., "Monitoring the Chest with Impedance", Chest, 64(5), (Nov. 1973), 597-603.

Viirola, H, et al., "Controlled growth of antimony-doped tin dioxide thin films by atomic layer epitaxy", Thin Solid Films, 251, (Nov. 1994), 127-135.

Viirola, H, et al., "Controlled growth of tin dioxide thin films by atomic layer epitaxy", Thin Solid Films, 249(2), (Sep. 1994), 144-149.

Visokay, M R, "Application of HfSiON as a gate dielectric material", Applied Physics Letters, 80(17), (Apr. 2002), 3183-3185.

Wang, L., et al., "Impedance based prediction of CHF admission precedes symptoms in heart failure patients", Heartrhythm : the official journal of the Heart Rhythm Society, 1(Suppl 1), Abstract 679, (2004), S213.

Wang, L., et al., "Prediction of CHF hospitalization by ambulatory intrathoracic impedance measurement in CHF patients is feasible using pacemaker or ICD lead systems", Pacing and Clinical Electrophysiology, 26(4 pt. II), Abstract 123, (Apr. 2003), 959.

Wang, Li, et al., "Multiple Sources of the Impedance Cardiogram Based on 3-D Finite Difference Human Thorax Models", IEEE Transactions on Biomedical Engineering, 42(2), (Feb. 1995), 141-148.

Wuerz, Richard C, et al., "Effects of prehospital medications on mortality and length of stay in congestive heart failure", Annals of Emergency Medicine, 21(6), (Jun. 1992), 669-74.

Yu, C., et al., "Changes in device based thoracic impedance in decompensating congestive heart failure", Circulation, 104(17 supplement),, Abstract 1994, (2001), II-419.

Yu, C. M., et al., "Correlation of device-based intra-thoracic impedance and patient fluid status during intravenous diuretic therapy in acute CHF", European Heart Journal, 23(Abstract Supplement), (2002), 158.

Yu, C., et al., "Device-based intra-thoracic impedance correlates with fluid status and provides automated prediction of CHF hospitalization", Journal of Cardiac Failure, 10(4 Suppl), Abstract 354, (2004), S113.

Yu, C., et al., "Early warning of CHF hospitalization by intra-thoracic impedance measurement in CHF patients with pacemakers", Pacing and Clinical Electrophysiology: Pace, 24(4 pt II), Abstract 19, (2002), 527.

Yu, C. M., et al., "Impedance measurements from implanted devices provide automated prediction of CHF hospitalization", European Heart Journal, 25(Supp), (Aug.-Sep. 2004), P27-27.

Yu, C. M., et al., "Intrathoracic impedance: A surrogate measure of fluid retention and predictor of hospitalization in patients with heart failure", Journal of the American College of Cardiology, 41(6 Supplement A), Abstract 1206-70, (2003), 210A.

Zellner, J. L., et al., "Bioimpedance: a novel method for the determination of extravascular lung water.", The Journal of Surgical Research, 48(5), (May 1990), 454-9.

Zhu, Q., et al., "Cardiac Rhythm Management System for Edema", U.S. Appl. No. 11/673,699, filed Feb. 12, 2007, 22 pgs.

Zima, E., "Intracardiac impedance in biventricular electrode configuration for left ventricular volume monitoring", European Heart Journal, 25(Supp), (Aug.-Sep. 2004), P165-165.

"European Application Serial No. 03786528.4, Communication Pursuant to Art, 94(3) EPC mailed Nov. 15, 2011",6 pgs.

"European Application Serial No. 03786528.4, Response filed Mar. 23, 2012 to Office Action mailed Nov. 15, 2011", 14 pgs.

"European Application Serial No. 11177888.6, European Search Report mailed Nov. 15, 2011", 5 pgs.

* cited by examiner

# ENHANCEMENTS TO THE DETECTION OF PULMONARY EDEMA WHEN USING TRANSTHORACIC IMPEDANCE

CROSS-REFERENCE TO RELATED APPLICATIONS

This application is a continuation of U.S. application Ser. No. 11/126,689, filed on May 11, 2005, now issued as U.S. Pat. No. 7,907,997, the benefit of priority of which is claimed herein, and which is incorporated herein by reference in its entirety.

This patent application is related to U.S. patent application Ser. No. 11/126,723, filed on May 11, 2005, entitled "IMPROVED SENSITIVITY AND SPECIFICITY OF PULMONARY EDEMA DETECTION WHEN USING TRANSTHORACIC IMPEDANCE," which is hereby incorporated by reference in its entirety.

TECHNICAL FIELD

This patent document pertains generally to medical systems, devices, and methods, and more particularly, but not by way of limitation, to medical systems, devices, and methods for the detection of pulmonary edema using thoracic impedance.

BACKGROUND

Variations in how much fluid is present in a person's thorax can take various forms and can have different causes. As an example, eating salty foods can result in retaining excessive fluid in the thorax, which is commonly referred to as "thoracic fluid," and elsewhere. Posture changes can also affect the amount of thoracic fluid. For instance, moving from supine to standing can shift intravascular fluid away from the thorax toward the lower extremities.

Another cause of fluid build-up in a person's thorax is pulmonary edema, which involves buildup of extravascular fluid in the lungs. In pulmonary edema, fluid accumulates in extracellular spaces, such as the spaces between lung tissue cells. One cause of pulmonary edema is congestive heart failure (CHF), which is also sometimes referred to as "chronic heart failure," or simply as "heart failure." CHF can be conceptualized as an enlarged weakened heart muscle. The impaired heart muscle results in poor cardiac output of blood. As a result of such poor blood circulation, blood tends to pool in blood vessels in the lungs and becomes a barrier to normal oxygen exchange. This intravascular fluid buildup, in turn, results in the extravascular fluid buildup mentioned above. Accordingly, pulmonary edema can be an indicative and important condition associated with CHF.

Pulmonary edema, if it exists, may present a medical emergency that requires immediate care. Although it can sometimes prove fatal, the outlook for people possessing pulmonary edema can be good upon early detection and prompt treatment of the same. If left untreated, pulmonary edema can lead to death.

Implantable medical devices (IMD) include, among other things, cardiac rhythm management (CRM) devices such as pacers, cardioverters, defibrillators, cardiac resynchronization therapy (CRT) or coordination devices, and drug delivery systems. Such devices are often used for providing a diagnosis, a therapy, or both a diagnosis and a therapy.

An IMD's detection scheme is typically characterized by its "sensitivity" and "specificity." Sensitivity generally refers to the ability of the detection scheme to effectively detect that which the caregiver desires the IMD to detect or treat. Sensitivity can be expressed as follows:

[Sensitivity=True Positives/(True Positives+False Negatives)] (Eq. 1)

Specificity generally refers to the ability of the detection scheme to avoid improperly treating that which the caregiver determines that the device should not treat. Specificity can be expressed as follows:

[Specificity=True Negatives/(True Negatives+False Positives)] (Eq. 2)

Ideally, an IMD would have both 100% sensitivity and 100% specificity. However, it is known in the art that for practical IMDs, there exists a tradeoff between sensitivity and specificity, such that no practical detection scheme can obtain the ideal.

Pulmonary edema is common in heart failure patients and, as discussed above, may be life threatening in many situations. Therefore, it is desirable to timely detect and treat pulmonary edema. Because of the potential severe (indeed life-threatening) consequences of failing to detect the presence of, and subsequently treat, pulmonary edema, it may be important that an IMD is configured to maximize sensitivity. At the same time, it may be important for such a device to possess a high level of specificity to avoid erroneous alerts and unneeded (and possibly harmful) treatment.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

DETAILED DESCRIPTION

Figure 1:
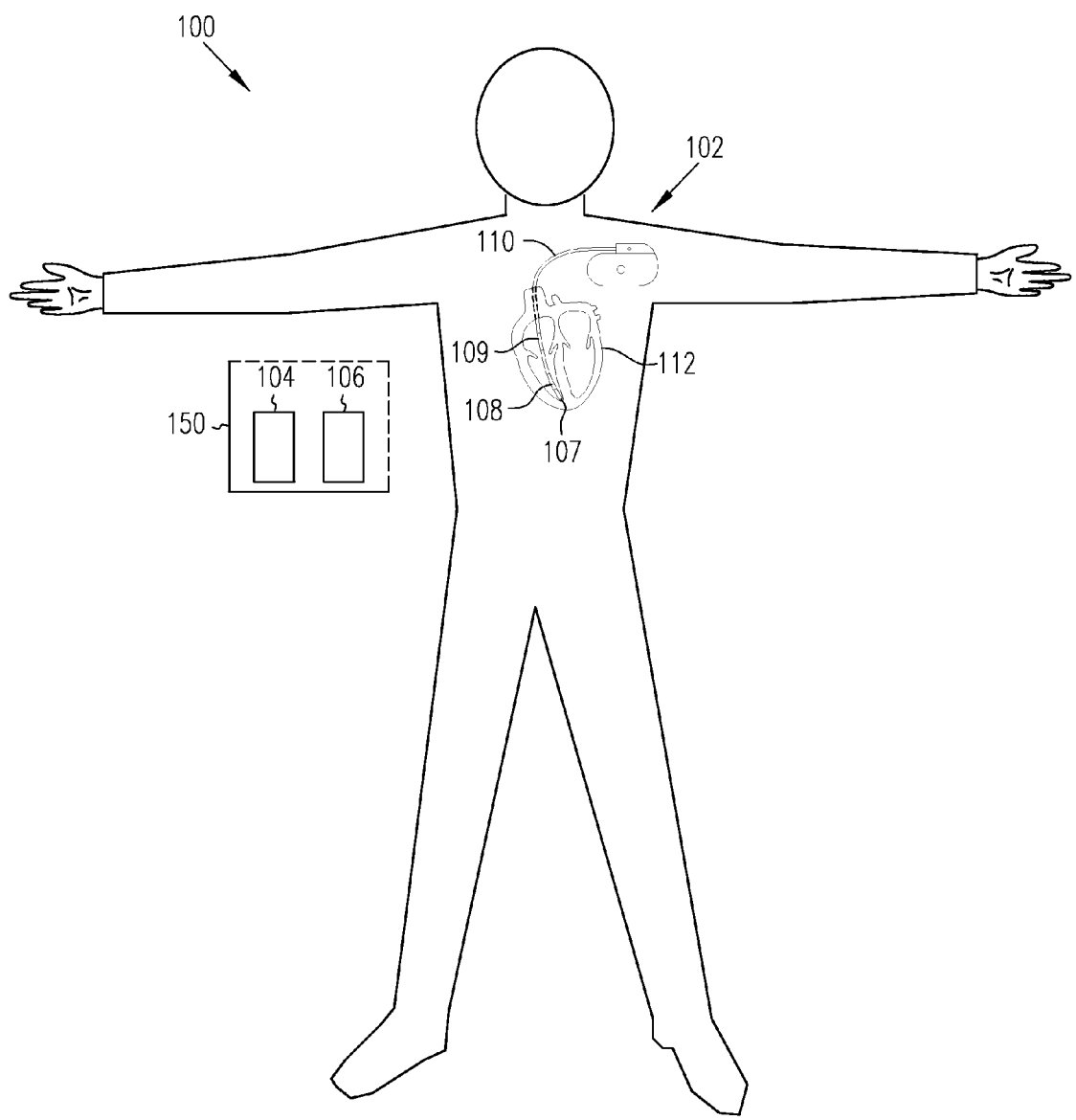
FIG. 1 is a schematic view illustrating portions of a system including an IMD and one or more external elements adapted to communicate with the IMD, the system is adapted to enhance the detection of pulmonary edema.

The following detailed description includes references to the accompanying drawings, which form a part of this detailed description. The drawings show, by way of illustration, specific embodiments in which the present systems, devices, and methods may be practiced. These embodiments, which are also referred to herein as "examples," are described in enough detail to enable those skilled in the art to practice the present systems, devices, and methods. The embodiments may be combined, other embodiments may be utilized, or structural, logical or electrical changes may be made without departing from the scope of the present systems, devices, and methods. It is also to be understood that the various embodiments of the present systems, devices, and methods, although different, are not necessarily mutually exclusive. For example, a particular feature, structure or characteristic described in one embodiment may be included with other embodiments. The following detailed description is, therefore, not to be taken in a limiting sense, and the scope of the present systems, devices, and methods are defined by the appended claims and their legal equivalents.

In this document: the terms "a" or "an" are used to include one or more than one; the term "or" is used to refer to a nonexclusive or, unless otherwise indicated; the terms "near-DC thoracic impedance signal(s)" (or simply "near-DC component") are defined to include thoracic impedance signals at frequencies less than the frequencies at which cardiac stroke and respiration components (of thoracic impedance signals) lie, which is typically understood to include signal frequencies from 0 Hz to about 0.05 Hz, inclusive (e.g., cardiac stroke and respiration components of thoracic impedance signals lie at frequencies greater than 0.05 Hz); the term "intravascular" includes the term "intracardiac"; the term "thorax" refers to a human subject's body between the neck and diaphragm; the term "subject" is used synonymously with the term "patient"; the term "determine" is used to mean 'to find out, detect, or come to a decision by investigation, reasoning, comparing, or calculation'; the term "user" includes a caregiver, a subject, a loved one or others who may ascertain or provide physiologic information, previous pulmonary edema parameter information, or patient symptom information to the present systems, devices, and methods; and the term "treatment" includes, among other things, a therapy directed to an underlying cause of an excessive thoracic fluid build-up or the excessive thoracic fluid build-up itself.

Furthermore, all publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

INTRODUCTION

Today, heart failure is a major cause of hospital admissions. Many of these admissions are due to fluid accumulation in the lungs as a result of pulmonary edema, which is challenging to treat and often goes unrecognized until a subject is critically ill. It is not unusual for subjects with heart failure to require hospitalization or urgent treatment at an emergency room or critical care unit. Approximately 30-40% of subjects with CHF are hospitalized every year. Further, CHF is a leading diagnosis-related group among hospitalized subjects over the age of 65. Morbidity and mortality of heart failure can potentially be lowered with accurate, timely detection and appropriate treatment of disease conditions in their early stages, such as upon early detection and treatment of pulmonary edema.

Early detection and treatment of pulmonary edema can reduce or eliminate the need for hospital admission of subjects with CHF. A reduction or elimination of the need for hospitalization results in lower health care costs. It is currently estimated that overall expenditures for management and treatment of heart failure may be as high as 24 billion dollars per year. Advantageously, the present systems, devices, and methods provide an accurate, early detection of pulmonary edema, and thereby provide a timely indication of CHF. As discussed, early warnings of heart failure may help avoid expensive hospitalizations and may preempt a subject from reaching a critically ill state.

EXAMPLES

Detection of pulmonary edema may be made by monitoring an impedance of a subject's thoracic cavity. In this way, a reduction in thoracic impedance indicates the presence of an increase in thoracic fluid. Conversely, fluid depletion in the thorax corresponds to an increase in the thoracic impedance sensed. In pulmonary edema, a reduction in thoracic impedance indicates an increase in the amount of fluid inside the subject's lungs.

The present systems, devices, and methods improve a sensitivity of pulmonary edema detection using, in addition to thoracic impedance, one or a combination of: physiologic information about the subject, at least one statistical parameter regarding the variability of the thoracic impedance, at least one parameter associated with a previous pulmonary edema episode, and patient symptom information about the subject. As will be discussed below, when the physiologic information, the at least one statistical parameter, the at least one previous parameter, or the patient symptom information point toward the presence of pulmonary edema, a (base) thoracic impedance threshold may be adjusted to increase detection sensitivity (to account for such information/parameter(s)).

The techniques for detecting pulmonary edema, as described herein, may be implemented in an IMD adapted to perform detection only or in an IMD configured to also deliver a therapy. In one example, the IMD is a cardiac rhythm management (CRM) device adapted to provide bradycardia pacing therapy, cardioversion/defibrillation therapy, drug therapy, or cardiac resynchronization therapy. Such therapy may be particularly useful since heart failure subjects with pulmonary edema may also benefit from, for example, resynchronization pacing which can improve cardiac function by causing the ventricles of a subject's heart to contract in a more coordinated manner. Examples of resynchronization devices are described in Kramer, et al., U.S. Pat. No. 6,574,506, entitled "SYSTEM AND METHOD FOR TIMING SYNCHRONIZED PACING," assigned to Cardiac Pacemakers, Inc., and hereby incorporated by reference in its entirety.

This document discusses, among other things, systems, devices, and methods that will be described in applications involving IMDs including, but not limited to, implantable CRM systems such as pacemakers, cardioverter/defibrillators, pacer/defibrillators, biventricular or other multi-site resynchronization or coordination devices, and drug delivery systems. However, the systems, devices, and methods described herein may also be employed in unimplanted devices, including, but not limited to, external pacemakers, cardioverter/defibrillators, pacer/defibrillators, biventricular or other multi-site resynchronization or coordination devices, monitors, programmers and recorders, whether such devices are used for providing detection, therapy, or both detection and therapy.

FIG. 1 is a schematic view illustrating portions of a system 100 that is capable of accurate, enhanced detection of pulmonary edema through utilization of one or a combination of: physiologic information about the subject, at least one statistical parameter regarding the variability of sensed thoracic impedance, a user-programmable thoracic impedance measurement detection level, at least one parameter associated with a previous pulmonary edema event, and patient symptom information about a subject, in addition to sensed thoracic impedance measurements. System 100 includes an implantable medical device (IMD) 102, such as a cardiac rhythm management (CRM) device, and a parameter collection device 150 including external elements such as an external user interface 104 or an external sensor 106. In the illustrative example of FIG. 1, IMD 102 is a battery-powered device that is implanted subcutaneously in a subject's chest or elsewhere and connected to electrodes 107, 108, 109 by one or more leadwires 110 associated with the subject's heart 112. In this example, external user interface 104 and external sensor 106 are adapted to wirelessly communicate with IMD 102.

Figure 2:
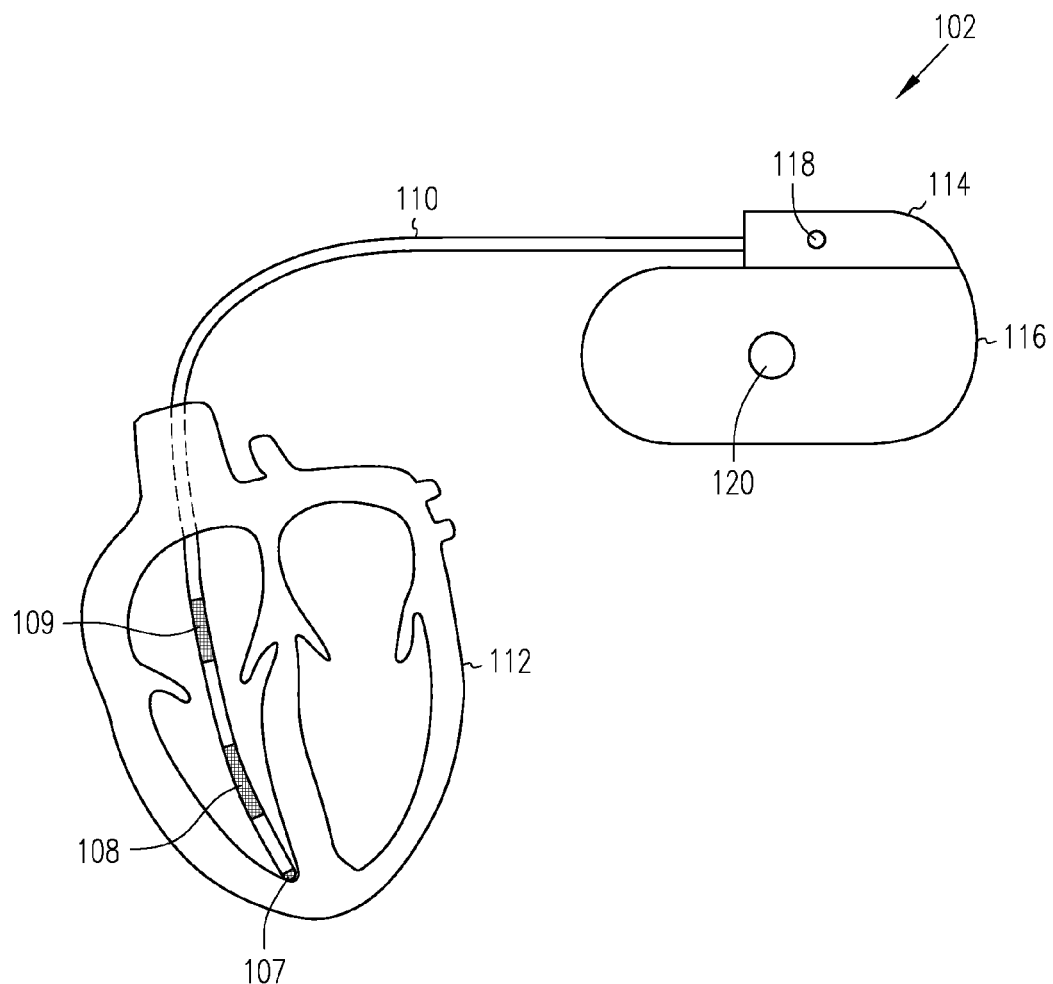
FIG. 2 is a schematic view illustrating an IMD suitable for use in a system adapted to enhance the detection of pulmonary edema.

FIG. 2 is a schematic view illustrating an IMD 102, such as a CRM device. In this example, IMD 102 is coupled to a heart 112 using one or more leadwires 110, such as a multi-electrode leadwire. In this example, the leadwire 110 includes a tip electrode 107, a distal ring electrode 108, and a proximal ring electrode 109, each of which is disposed in the right side of heart 112. In this example, each of the tip electrode 107, the distal ring electrode 108, and the proximal ring electrode 109 is independently electrically connected to a corresponding separate electrically conductive terminal within an insulating header 114. The header 114 is affixed to a hermetically sealed housing 116, which may be formed from a conductive metal, such as titanium, and which carries electronic components of the IMD 102. The housing 116 may be substantially covered over its entire surface by a suitable insulator, such as silicone rubber. In this example, header 114 includes a header electrode 118, and housing 116 includes a housing electrode 120.

In one example, thoracic impedance is sensed by delivering a test current between: (1) at least one of the ring electrodes 108 or 109; and (2) the housing electrode 120, and a resulting responsive voltage is measured across the tip electrode 107 and the header electrode 118. When the IMD 102 is pectorally implanted at some distance away from the heart 112, this electrode configuration injects the test current over a substantial portion (but typically not the entire portion) of a subject's thorax, such that when the resulting voltage measurement is divided by the test current magnitude, it yields an indication of thoracic impedance. Using different electrodes for delivering the current and for measuring the responsive voltage reduces the component of the measured impedance signal that results from ohmic losses at the tissue-sense electrode interface and in the leadwires to the test current delivery electrodes.

While such a "four-point" probe (probe utilizing four electrodes) is useful, it is not required. In other examples, a "three-point" probe (probe utilizing three electrodes, with one electrode used for both test current delivery and responsive voltage measurement), or a "two-point" probe (probe utilizing two electrodes, each electrode used for both test current delivery and responsive voltage measurement) are used. Moreover, other electrode combinations could alternatively be used to implement a four-point probe. The above described four-point probe provides an illustrative example of one suitable four-point probe configuration. Other illustrative examples of four-point probe circuits for sensing thoracic impedance signals from a subject, are described in Hauck et al., U.S. Pat. No. 5,284,136 entitled, "DUAL INDIFFERENT ELECTRODE PACEMAKER," which is assigned to Cardiac Pacemakers, Inc., and herein incorporated by reference in its entirety, including its description of performing thoracic impedance measurements.

Figure 3:
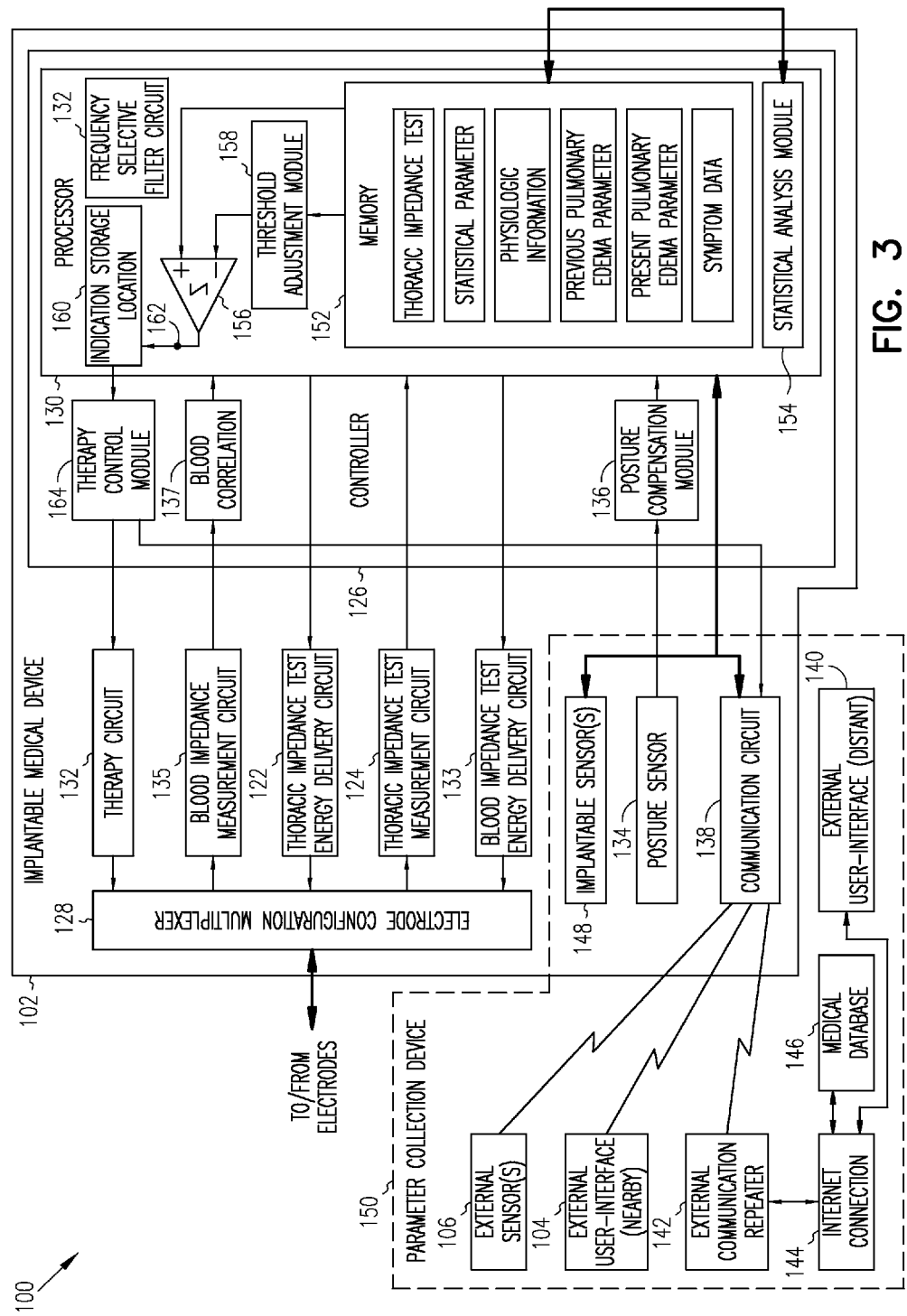
FIG. 3 is a schematic diagram illustrating portions of a system adapted to enhance the detection of pulmonary edema.

FIG. 3 is a schematic diagram illustrating portions of a system 100 capable of accurate, enhanced detection of pulmonary edema using, in addition to sensed thoracic impedance, one or a combination of: physiologic information about a subject, at least one statistical parameter regarding the variability of the sensed thoracic impedance, a user-programmable thoracic impedance detection level, at least one parameter associated with a previous pulmonary edema event, and patient symptom information about the subject. In this example, system 100 includes a hermetically sealed IMD 102 and a programmer or other external user interface 104 or 140. In this example, an intracardiac leadwire 110 is a catheter connected to IMD 102, with a distal portion intravascularly introduced into a subject's heart 112.

The example of FIG. 3 includes a thoracic impedance test energy delivery circuit 122 that, together with a thoracic impedance measurement circuit 124, senses a thoracic impedance signal from the subject. In accordance with instructions provided by a controller 126, an electrode configuration multiplexer 128 couples the thoracic impedance test energy delivery circuit 122 and the thoracic impedance measurement circuit 124 to one or more appropriate electrodes associated with the subject's thorax. By way of such electrodes, the thoracic impedance measurement circuit 124 may accurately sense a thoracic impedance signal from the subject. In some examples, the multiplexer 128 may be coupled to a heart signal sensing circuit that includes a sense amplifier or other circuits for detecting from one or more particular electrodes intrinsic electrical heart signals that include electrical depolarizations corresponding to heart contractions. In this example, the multiplexer 128 is also coupled to a therapy circuit 132, such as a pulse delivery circuit for delivering therapy (e.g., pacing, resynchronization, ATP, cardioversion, or defibrillation) by way of one or more electrodes 107, 108, or 109. In one example, therapy is provided to the subject in response to instructions provided by the controller 126 and received by the therapy circuit 132. In another example, a timing circuit is used in the delivery of the therapy to the subject.

Other illustrative examples of electrode configurations and circuits for sensing thoracic impedance signals from a subject, are described in Hartley et al., U.S. Pat. No. 6,076,015 entitled, "RATE ADAPTIVE CARDIAC RHYTHM MANAGEMENT DEVICE USING TRANSTHORACIC IMPEDANCE," which is assigned to Cardiac Pacemakers, Inc., and herein incorporated by reference in its entirety, including its description of performing thoracic impedance measurements. The Hartley et al., U.S. Pat. No. 6,076,015, uses thoracic impedance signals to obtain respiration signals. In contrast, the systems, devices, and methods described herein use thoracic impedance signals to obtain an indication of a fluid amount within the subject's thorax; however, both thoracic fluid amount and respiration signals are obtainable using the thoracic impedance measurement techniques described in Hartley et al. In one example of the present systems, devices, and methods, the thoracic fluid amount is obtained from a lower frequency (e.g., a "near-DC" (less than about 0.05 Hz)) portion of the thoracic impedance signal rather than the frequencies of the respiration signal described in Hartley et al.

In this document, the near-DC component of the thoracic impedance signal, refers to the frequencies below which respiration and cardiac contractions significantly influence the thoracic impedance signal (e.g., at least an order of magnitude lower than the respiration component). In one example, the near-DC component of the thoracic impedance signal refers to signal frequencies below a cutoff frequency having a value of about 0.05 Hz, such as at signal frequencies between about 0 Hz and about 0.05 Hz, because the cardiac stroke and respiration components of the thoracic impedance signal lie at higher frequencies. Such near-DC frequencies may include DC frequencies.

In varying examples of the system 100, the controller 126 may include a processor 130 or any other means capable of sequencing through various control states and having executable instructions stored in an associated memory storage device, a microsequencer, or a state machine. In the illustrative example of FIG. 3, the controller 126 includes a processor 130. In one example, the processor 130 performs any filtering or other signal processing needed to extract the near-DC component from the sensed thoracic impedance signal by processing a stored sequence of executable instructions. In this example, the filtering or signal processing is performed by dedicated filtering hardware (e.g., a frequency selective filter circuit 132). In yet another example, the filtering or signal processing is performed in an external device such as an external user interface 104 or 140. Although the processor 130 is illustrated as being integrated within the IMD 102 in FIG. 3, the processor 130 or other sequencing means may also be located external to the IMD 102.

As discussed above, variations in how much fluid is present in the subject's thorax can take various forms and can have different causes. Beyond pulmonary edema and eating salty foods for example, posture changes may also affect an amount of fluid the subject has in his/her thorax. For example, moving from a supine position to a standing position can shift intravascular fluid away from the subject's thorax toward the subject's lower extremities thereby decreasing the amount of thoracic fluid present. For this reason, the system 100 of FIG. 3 includes a posture sensor 134 adapted to sense the subject's posture. In one example, the posture sensor 134 senses a "posture signal" which is indicative of the subject's then-current posture. A different posture signal is provided by posture sensor 134 for different postures (e.g., a posture signal for upright postures differs from a posture signal for recumbent postures). One example of a suitable posture sensor 134 commercially available is a two-axis accelerometer, such as Model No. ADXL202E, manufactured by Analog Devices, Inc. of Norwood, Mass., USA; however, other posture sensors may also be used without departing from the scope of the present systems, devices, and methods.

In this example, the posture signal sensed by the posture sensor 134 is used to remove a posture component from the sensed thoracic impedance signal resulting in a "posture-compensated" thoracic impedance signal. In one example, a posture compensation module 136 may be used to remove the posture component using the posture signal corresponding to the then-current posture sensed by the posture sensor 134. For example, the posture compensation module 136 may numerically increase a sensed thoracic impedance signal value when the posture sensor 134 senses the subject's then-current posture as being supine. The rationale being that the subject's supine orientation may have affected the amount of fluid in the subject's thorax and thus, the sensed thoracic impedance signal value. The timing circuit may be used to assign each sensed thoracic impedance signal to the then-current posture signal. In this example, the timing circuit is used in conjunction with memory 152 to store a thoracic impedance signal sensed at time 1 with a posture signal sensed at time 1, a thoracic impedance signal sensed at time 2 with a posture signal sensed at time 2, . . . , a thoracic impedance signal sensed at time N with a posture signal sensed at time N.

The thoracic impedance signal may also be affected by confounding factors other than the amount of fluid present in the thorax. One such confounding factor is any change in blood resistivity. Blood resistivity changes as a function of hematocrit in the blood. The hematocrit (Ht) or packed cell volume (PCV) is the proportion of blood that is occupied by red blood cells. It is typically between 0.35 (35%) and 0.52 (52%), and is slightly higher, on average, in males than in females. For example, when the subject is dehydrated, there will be less fluid in the subject's blood. Therefore, the subject's hematocrit level will increase, that is, the subject's blood will include a higher percentage of other components, such as insulative red blood cells. This will increase the blood resistivity, which, in turn may affect the sensed thoracic impedance signal even though it is not necessarily associated with the extravascular fluid accumulation of pleural effusion or pulmonary edema. Other factors that are believed to possibly influence blood resistivity include the subject's electrolyte level, certain medications in the blood, proteins in the blood, or blood gas concentrations.

As an illustrative example, the above change in hematocrit percentage from 35% to 52% may correspond to a change in resistivity from about 140 $\Omega\cdot$cm to about 200 $\Omega\cdot$cm. Such changes in blood resistivity may influence the sensed thoracic impedance. This may confound an extravascular thoracic fluid amount determination using the sensed thoracic impedance, unless the extravascular thoracic fluid amount determination is corrected for such variations in blood resistivity, if any. Measurement of variations in blood resistivity is typically affected by the frequency of the excitation signal that is used. At higher excitation frequencies, blood cells typically become more resistive.

Accordingly, the system in FIG. 3 illustrates a blood impedance measurement circuit 135. The blood impedance measurement circuit 135 receives a blood impedance measurement from electrodes that are associated with blood (and preferably blood in the thorax) such as in response to a delivery of test energy by a blood impedance test energy delivery circuit 133. In one example, the blood impedance measurement circuit 135 and the blood impedance test energy delivery circuit 133 are configured similar to the thoracic impedance measurement circuit 124 and the thoracic impedance test energy delivery circuit 122 respectively, as discussed above, except for possibly being connected to different electrodes. Using the blood impedance measurement, the controller 126 executes a sequence of instructions to compute a blood resistivity correction 137. In this example, the blood resistivity correction 137 is applied to the sensed thoracic impedance signal that is received by the processor 130. This yields a "blood resistivity-compensated" thoracic impedance signal.

In FIG. 3, the thoracic impedance test energy delivery circuit 122 is illustrated separately from the blood impedance test energy delivery circuit 133 to assist in conceptualization. In practice however, these circuits, or portions thereof, may be combined. The combined circuit may be coupled to different electrodes for delivering the thoracic impedance test energy than for delivering the blood impedance test energy. Similarly, in FIG. 3, the thoracic impedance measurement circuit 124 is illustrated separately from the blood impedance measurement circuit 135 to further assist in conceptualization. In practice however, these circuits, or portions thereof, may be combined as well. The combined circuit may be coupled to different electrodes for measuring the responsive voltages for the thoracic and blood impedance measurements. Illustrative examples of performing such thoracic and blood impedance measurements are described in Stahmann et al., U.S. patent application Ser. No. 10/921,503, entitled "THORACIC IMPEDANCE DETECTION WITH BLOOD RESISTIVITY COMPENSATION," which is assigned to Cardiac Pacemakers, Inc., and herein incorporated by reference in its entirety.

Once established, the sensed thoracic impedance signal or variation thereof (e.g., near-DC thoracic impedance signal, posture-compensated thoracic impedance signal, or blood resistivity-compensated thoracic impedance signal) may be compared to a thoracic impedance threshold value to determine whether such thoracic impedance signal is indicative of pulmonary edema. In the example of FIG. 3, a comparator 156 compares the sensed thoracic impedance signal or variation thereof to a thoracic impedance threshold. In this example, and as discussed above, a reduction in a thoracic impedance signal indicates the presence of an increase in thoracic fluid. It follows that a thoracic impedance signal indicative of pulmonary edema is a signal which is numerically less than or substantially equal to a thoracic impedance threshold value.

In one example, the thoracic impedance threshold compared against is a base thoracic impedance threshold. The base thoracic impedance threshold may include a thoracic impedance boundary established to differentiate between thoracic impedance signals that are non-indicative of pulmonary edema and thoracic impedance signals that are indicative of pulmonary edema. As an example, a sensed thoracic impedance signal or variation thereof numerically less than, or substantially equal to, the base thoracic impedance threshold may indicate pulmonary edema is present, while a thoracic impedance signal numerically greater than the base thoracic impedance threshold may indicate pulmonary edema is not present. In one example, the thoracic impedance threshold is subject specific (e.g., individualized to the patient) and determined by a caregiver, such as at the time of implantation. In another example, the base thoracic impedance threshold is nonsubject-specific (e.g., a standardized threshold). In this example, the base thoracic impedance threshold is programmed into IMD 102, such as processor 130.

In another example, the thoracic impedance threshold is an adjusted thoracic impedance threshold value which represents an increase in detection sensitivity of the presence of pulmonary edema over the base thoracic impedance threshold. The adjusted thoracic impedance threshold value is generated from the base thoracic impedance threshold in addition to information sensed or received by a parameter collection device 150. As an example, information sensed or received by parameter collection device 150 that is indicative of the presence of pulmonary edema results in the adjusted thoracic impedance threshold being numerically increased from the base thoracic impedance value. In a similar manner, but numerically opposite, information sensed or received by parameter collection device 150 that points away from the presence of pulmonary edema decreases (or leaves unchanged) the thoracic impedance threshold from the base thoracic impedance value. In this example, a threshold adjustment module 158 computes the adjusted thoracic impedance threshold value using the information sensed or received by parameter collection device 150. In a further example, the adjusted thoracic impedance threshold may be user-programmed into IMD 102.

In another example, although not illustrated, the sensed thoracic impedance signal or variation thereof is changed using the information sensed or received by parameter collection device 150. As an example, information sensed or received by parameter collection device 150 that points toward the presence of pulmonary edema decreases the sensed thoracic impedance signal value. Conversely, information sensed or received by parameter collection device 150 that points away from the presence of pulmonary edema increases (or leaves unchanged) the sensed thoracic impedance signal value.

Comparing the sensed thoracic impedance signal or variation thereof to the base or adjusted thoracic impedance threshold value provides an indication (which can be stored at an indication storage location 160) of whether the thoracic fluid present in the subject is indicative of pulmonary edema (e.g., a thoracic impedance less than or substantially equal to a thoracic impedance threshold is deemed indicative of pulmonary edema, while a thoracic impedance greater than the thoracic impedance threshold is deemed non-indicative of pulmonary edema). In the example of FIG. 3, a binary indication at node 162 controls a therapy control module 164 that responsively adjusts or initiates a therapy to the subject, such as cardiac rhythm management therapy, dietary therapy, or breathing assistance therapy. In one example, the therapy control module 164 is integrated with IMD 102. In another example, the therapy control module 164 is located externally to IMD 102, such as integrated with an external user-interface 104 or 140. In this example, the binary indication at node 162 is provided to a communication circuit 138, which is capable of communicating to the subject or other user, via external user interface 104 or 140, information about whether pulmonary edema is present.

The parameter collection device 150 shown is adapted to receive information from a user or sense information internally via sensor 148 (which may include posture sensor 134) or externally via sensor 106 and provide such information to the IMD 102. In one example, the parameter collection device 150 is adapted to sense or receive physiologic information about the subject and provide such information to system 100. The physiologic information collected by system 100, such as parameter collection device 150, may include one or more of: at least one heart sound, at least one lung sound, a respiratory pattern, a weight of the subject, a neurohormone level, a creatinine level, and a heart wall motion, which is used to ascertain a cardiac dyskinetic condition. Illustrative examples of techniques for ascertaining the cardiac dyskinetic condition are described in Yu et al. U.S. Patent Application Number 2003/0105496,entitled "CARDIAC RESYNCHRONIZATION SYSTEM EMPLOYING MECHANICAL MEASUREMENT OF CARDIAC WALLS," which is assigned to Cardiac Pacemakers, Inc., and which is incorporated herein by reference in its entirety.

In another example, the parameter collection device 150 is a previous or present parameter device. The previous parameter information sensed or received by system 100 may include one or more parameter associated with a previous pulmonary edema event (e.g., pulmonary edema event occurring in the past) including: a previous thoracic impedance, a previous physiologic parameter, a previous environmental parameter, a previous compliance parameter, or a previous patient symptom parameter. The present parameter information sensed or received by system 100 may include one or more present parameter selected from a group consisting essentially of: a present physiologic parameter, a present environmental parameter, a present compliance parameter, and a present patient symptom parameter.

In a further example, the parameter collection device 150 is a patient symptom device. The one or more patient symptom sensed or received by system 100 may be selected from a patient symptom group consisting essentially of: a shortness of breath, a difficulty breathing, at least one wheeze, at least one cough, a feeling of anxiety, a feeling of restlessness, an excessive level of perspiration, an indication of pallor, a nasal flaring, a decreased level of awareness, and an increased heart rate.

In the example of FIG. 3, the IMD 102 carries various electrical components, such as the communication circuit 138, which is capable of wirelessly communicating with a communication circuit of the external user interface 104. In another example, the communication circuit 138 wirelessly communicates with a communication circuit of (distant) external user interface 140 by way of nearby communication repeater 142. In this example, the repeater 142 is coupled to the external user interface 140 by way of Internet connection 144. Also in this example, the communication circuit 138 of IMD 102 is communicatively coupled to a communication circuit of the external sensor 106. The IMD 102 may additionally or alternatively include the implantable sensor 148 therewithin or implanted nearby and coupled thereto.

In the example of FIG. 3, the processor 130 includes a statistical analysis module 154. The statistical analysis module 154 is programmed to determine at least one statistical parameter regarding the variability of the thoracic impedance signal or variation thereof and is selected from a statistical group consisting essentially of: a standard deviation and a variance. The at least one statistical parameter can be used by the processor 130 in the determination of the pulmonary edema indication.

In varying examples, the system 100 includes at least one memory 152 that is capable of storing information sensed or received by parameter collection device 150, the thoracic impedance measurement circuit 124, or the blood impedance measurement circuit 135. In the example of FIG. 3, the memory 152 is capable of storing one or a combination of: the sensed thoracic impedance signal or variation thereof, the physiologic information about the subject, the at least one statistical parameter regarding the variability of the thoracic impedance, a user-programmable thoracic impedance measurement detection level, the at least one parameter associated with a previous or present pulmonary edema event, and the patient symptom information about the subject.

In this example, the memory 152 is also adapted to store weights (e.g., Weight 1, Weight 2, . . . , Weight N). Each weight corresponding to a type of information sensed or received by parameter collection device 150. Each weight may be numerically different, such as the numerically greatest weight corresponds to a type of information sensed or received which points towards a greatest likelihood of (e.g., having the strongest correlation with) a pulmonary edema indication. In a similar manner, the numerically lowest weight corresponds to a type of information collected which points towards the least likelihood of (e.g., having the weakest correlation with) a pulmonary edema indication. In another example, the weight values depend on cross-correlation between two or more different types of data. As an illustrative example, parameters A and B may each have weights of 0.1 when such parameters are individually used by processor 130 in determining the pulmonary edema indication. However, when such parameters are both used by processor 130 in determining the pulmonary edema indication, A has a weight of 0.5 and B has a weight of 0.2. In sum, examples exists in which the weight values depend on cross-correlation between two or more different types of data. In yet another example, the weights are obtained from historical information of one or more subjects previously diagnosed with pulmonary edema. In such an example, the historical information is stored in electronic medical database 146 coupled to Internet connection 144 and thereby received by processor 130.

FIG. 3 illustrates one conceptualization of various circuits, sensors, devices, or modules which are implemented either in hardware or as one or more sequences of steps carried out on a microprocessor or other controller. Such circuits, sensors, devices, or modules are illustrated separately for conceptual clarity; however, it is to be understood that the various circuits, sensors, devices, or modules of FIG. 3 need not be separately embodied, but may be combined or otherwise implemented, such as in software or firmware.

Figure 4:
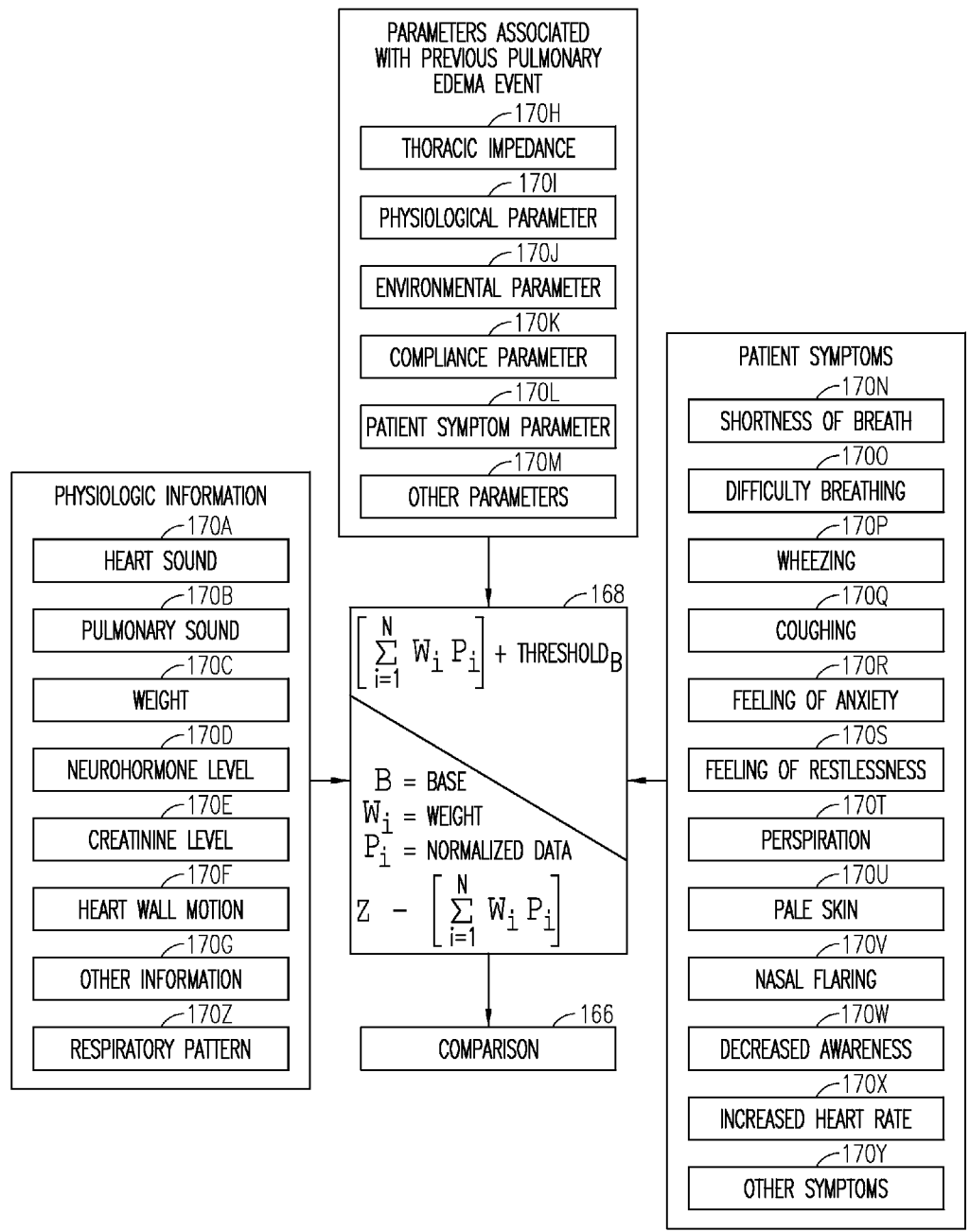
FIG. 4 is a chart illustrating physiologic parameters, parameters associated with a previous pulmonary edema event, and patient symptom parameters, at least one of which is used by a system to enhance the detection of pulmonary edema.

FIG. 4 is a chart illustrating physiologic information, parameters associated with a previous pulmonary edema event (e.g., a pulmonary edema event which occurred in the past), and patient symptom information (collectively hereinafter referred to as "pulmonary edema related factors"), at least one of which is used by the present systems, devices, and methods to enhance pulmonary edema detection in a subject. In one example, one or more pulmonary edema related factor is used to adjust a base thoracic impedance threshold (see e.g., FIG. 6). In another example, one or more pulmonary edema related factor is used to adjust a sensed thoracic impedance signal (or variation thereof) 168. The adjustment to the base thoracic impedance threshold or sensed thoracic impedance signal may include, at least in part, a normalization of the pulmonary edema related factors 170A-Z sensed or received (e.g., to obtain $P_i$). In another example, the adjustment includes a scaling of each normalized pulmonary edema related factor 170A-Z by a corresponding weight, (e.g., $W_i$), and summing the resulting products.

Figure 6:
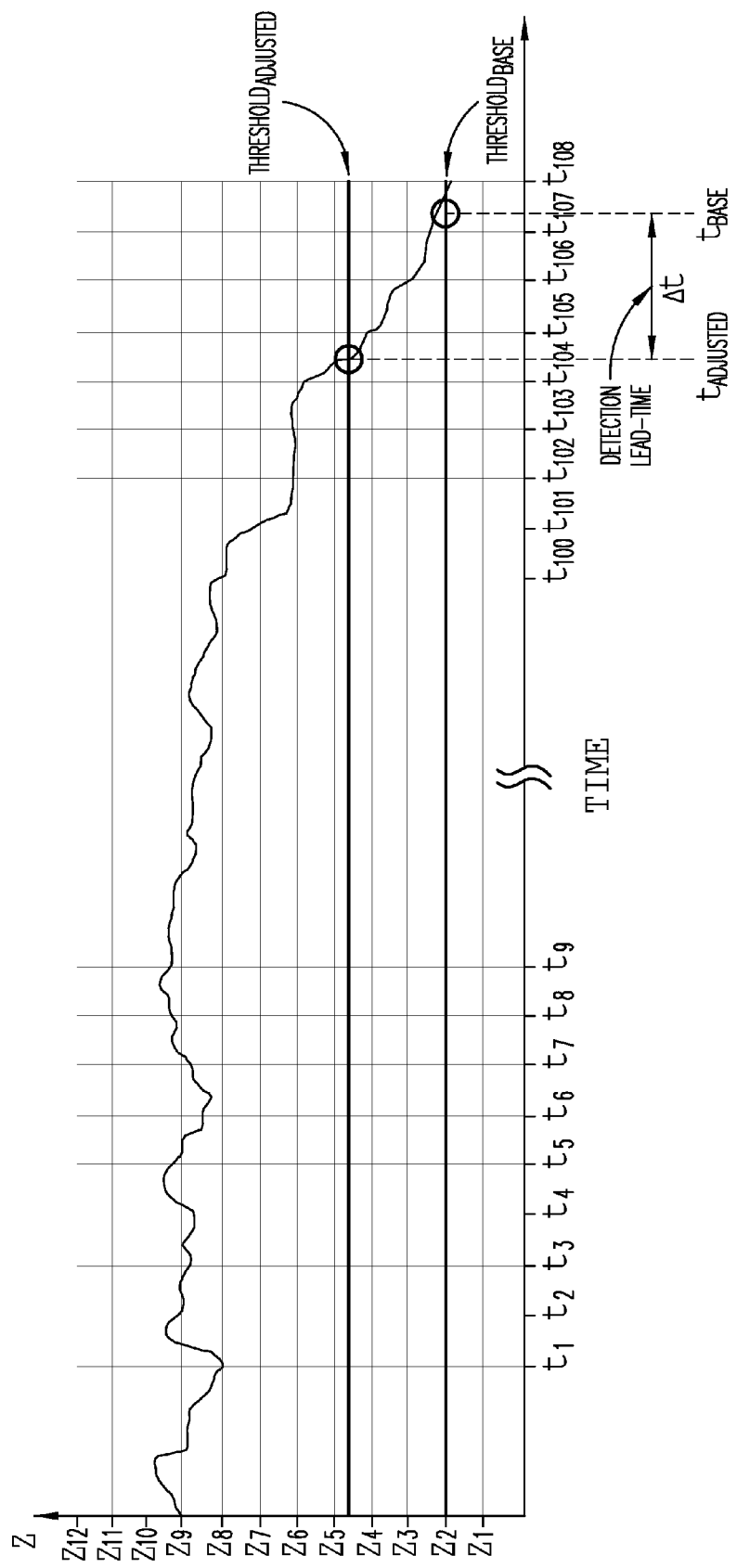
FIG. 6 is a graph illustrating a detection lead-time provided by a system adapted to enhance the detection of pulmonary edema.

In the illustrative chart of FIG. 4, a comparison at 166 between the sensed thoracic impedance signal (or variation thereof) and a base or adjusted thoracic impedance threshold takes place (see e.g., FIG. 6). Using the comparison, a pulmonary edema indication may be determined by processor 130.

In one example, a subject's heart sounds (for example, heart sounds referred to in the art as $S_1$, $S_2$, and particularly the heart sound referred to in the art as $S_3$) are used as a pulmonary edema related factor 170A. In one example, the heart sounds are measured by an implantable accelerometer, microphone or other implantable sensor 148, such as by using the systems and methods described in Lincoln et al. U.S. Pat. No. 6,665,564, entitled "CARDIAC RHYTHM MANAGEMENT SYSTEM SELECTING A-V DELAY BASED ON INTERVAL BETWEEN ATRIAL DEPOLARIZATION AND MITRAL VALVE CLOSURE," or the systems and methods described in Lincoln et. al. U.S. patent application Ser. No. 10/099,865, entitled "CARDIAC RHYTHM MANAGEMENT SYSTEM AND METHOD USING TIME BETWEEN MITRAL VALVE CLOSURE AND AORTIC EJECTION," each of which is assigned to Cardiac Pacemakers, Inc., and the disclosure of each of which is incorporated herein by reference in its entirety, including its description of heart sound detection. In another example, the heart sounds are measured by a caregiver while the subject is lying on his/her left side, and a numerical value indicative of a heart sound frequency or amplitude is input into parameter collection device 150, specifically external user interface 104 or 140, by the caregiver or other user. An increase in certain heart sound, such as $S_3$, frequency or amplitude may correlate to an indication of pulmonary edema.

In another example, the subject's changed pulmonary (lung) sounds (e.g., increased rales) is used as a pulmonary edema related factor 170B. In one example, the changed pulmonary sounds are measured by an implantable sensor 148, which may include a microphone, accelerometer, or other like sound detector. In another example, the subject, caregiver, or other user enters an indication of the degree of increased frequency or amplitude of the rales into external user interfaces 104 or 140 of parameter collection device 150. An increase in the frequency or amplitude of rales may correlate to an indication of pulmonary edema.

In another example, the subject's weight is used as a pulmonary edema related factor 170C. In one example, the subject's weight is measured by an external sensor 106 including a scale coupled to a wireless communication circuit which is capable of communicating with the communication circuit 138 of IMD 102. In another example, the subject's weight is measured on an external scale, and manually input by the subject, caregiver or other user into external user interface 104 or 140, and wirelessly communicated to communication circuit 138 of IMD 102. In another example, the subject weighs him/herself every morning at approximately the same time, such as before breakfast. An increase in weight may correlate to an indication of pulmonary edema since changes in heart failure status can cause both pulmonary edema and weight gain via peripheral edema.

In another example, the subject's neurohormone level (particularly the neurohormone level referred to in the art as brain (also known as "B-type") natriuretic peptide (BNP)) is used as a pulmonary edema related factor 170D. In one example, the subject's BNP level is measured by an external blood test, and an indication of the BNP level is thereafter entered into parameter collection device 150 by a user at the external user interface 104 or 140. In another example, the subject's BNP level is measured by an implantable sensor 148 or an external (e.g., transdermal) sensor 106. BNP is a chemical released by the subject's body in response to left ventricular stress. An increase in BNP may correlate to an indication of pulmonary edema. Serum levels of BNP can help identify CHF as the origin of dyspnea, which is commonly referred to "shortness of breath." Serum levels of BNP>500 pg/ml are most consistent with CHF. Atrial natriuretic peptide (ANP), a measure of atrial stress, may also be useful in determining the presence of pulmonary edema.

In another example, the subject's creatinine level is used as a pulmonary edema related factor 170E. In one example, the subject's creatinine level is measured by an external blood test, and an indication of the creatinine level is thereafter entered into parameter collection device 150 by the caregiver or other user at external user interfaces 104 or 140. In another example, the subject's creatinine level is measured by an implantable sensor 148 or an external sensor 106. Creatinine is a chemical released by the subject's kidneys in response to reduced renal blood flow. An increase in creatinine may correlate to an indication of pulmonary edema since changes in heart failure status can cause both pulmonary edema and an increase in creatinine.

In another example, the subject's heart wall motion is used as a pulmonary edema related factor 170F. During a cardiac cycle, each region of a ventricular endocardial wall undergoes a cycle of inward and outward displacement. In one example, each regional displacement cycle can be represented by a regional displacement curve that includes displacement magnitude plotted over time from the start to the end of a cardiac cycle interval. Because these displacements curves are periodic, they may be analyzed in the frequency domain to quantify the phase relationship between curves independent of the displacement magnitude and heart rate. Each regional displacement curve may be modeled as a wave with period equal to the cardiac cycle interval, which can be used as the fundamental frequency in a Fourier analysis. The time at which the center of this wave occurs during the cardiac cycle interval can be a function of the fundamental frequency phase angle. It is near 180° when centered in the middle of the cycle, 0-180° if it is shifted earlier, and 180-360° if it is shifted later. Inverted and triphasic displacement curves (e.g., with paradoxical wall motion) have phase angles near the end (360°) or start (0°) of the cycle. With this method, a degree of asynchrony between two regional displacement curves may be represented by the difference between their respective phase angles. Phase differences near 0° indicate near-perfect synchrony, while a difference of 180° defines maximal asynchrony. In another example, the subject's heart wall displacement is detected by performing an echocardiogram or other imaging measurement, and an indication of the heart wall synchrony or asynchrony is entered into parameter collection device 150 by the caregiver or other user at external user interfaces 104 or 140. In another example, the subject's heart wall displacement is sensed by an implantable sensor 148 or electrodes 107, 108, or 109. A determination that the regions of the endocardial wall are not moving in a coordinated manner may correlate to an indication of pulmonary edema.

In another example, the subject's respiratory pattern is used as a pulmonary edema related factor 170Z. The subject's respiratory pattern includes rapid breathing (tachypnea), rapid-shallow breathing, apnea, periodic breathing, Cheyne-stokes respiration, and other sleep-disordered breathing. In one example, the respiratory pattern is sensed via trans-thoracic impedance in an IMD 102. As an example, an increase in the subject's respiratory pattern (e.g., number of breaths/unit time) may correlate to an indication of pulmonary edema.

In another example, the subject's shortness of breath while sleeping (e.g., paroxysmal nocturnal dyspnea) is used as a pulmonary edema related factor 170N. In one example, paroxysmal nocturnal dyspnea is measured by implantable sensors 148, including a respiration sensor to detect shortness of breath and a sleep detector. One example of a sleep detector is described in Carlson et al. U.S. Pat. No. 6,678,547, entitled "CARDIAC RHYTHM MANAGEMENT SYSTEM USING TIME-DOMAIN HEART RATE VARIABILITY INDICIA," which is assigned to Cardiac Pacemakers, Inc., and which is incorporated herein by reference in its entirety, including its description of a sleep detector. In another example, the subject, caregiver or other user enters an indication of the degree of paroxysmal nocturnal dyspnea (e.g., frequency of respiration while sleeping) into external user interfaces 104 or 140 of IMD 102. An increase in paroxysmal nocturnal dyspnea may correlate to an indication of pulmonary edema.

In another example, the subject's shortness of breath while lying down (e.g., orthopnea) is used as a pulmonary edema related factor 170N. In one example, orthopnea is measured by implantable sensor 148, including a respiration sensor (e.g., an impedance sensor) to detect the shortness of breath and a posture sensor (e.g., an accelerometer). In another example, the subject, caregiver or other user enters an indication of the degree of orthopnea (e.g., frequency of respiration while lying down) into external user interface 104 or 140 of IMD 102. An increase in orthopnea may correlate to an indication of pulmonary edema.

In another example, the subject's difficulty breathing is used as a pulmonary edema related factor 170O. In one example, breathing difficulties are measured by one or more external blood tests (e.g., blood test including arterial blood gases or measurement of blood oxygen saturation), and an indication of the breathing difficulty is input into parameter collection device 150 by the caregiver or other user at external user interface 104 or 140. In another example, an indication of breathing difficulty is entered into parameter collection device 150 by the subject at external user interface 104 or 140 based on a sensation of difficult or uncomfortable breathing experienced by the subject. In some circumstances, a small degree of breathing difficulty may be normal. Severe nasal congestion is an example. Strenuous exercise, especially when a person does not exercise regularly, is another example of when a small degree of breathing difficulty may be normal. In many situations, however, difficulty breathing (which, in one example, is indicated by a low blood oxygen level) may correlate to an indication of pulmonary edema.

In another example, the subject's wheezing is used as a pulmonary edema related factor 170P. In one example, the subject's wheezing is measured by an implantable sensor 148, which may include a microphone, accelerometer, or other like sound detector. In another example, the subject, caregiver or other user enters an indication of the degree of wheezing, such as the degree of increased amplitude or duration of wheezing, into external user interfaces 104 or 140 of the parameter collection device 150. Wheezing is typically a high-pitched whistling sound produced by air flowing through narrowed breathing tubes, especially the smaller ones deep in the lung. Wheezing may be present during either inspiration (breathing in) or exhalation (breathing out). An increase in the amplitude or duration of wheezing may correlate to an indication of pulmonary edema.

In another example, the subject's "night cough" (or cough while lying down) is used as a pulmonary edema related factor 170Q. In one example, the night cough is measured by an implantable sensor 148 to detect the cough and a clock, a sleep detector, or a posture detector to respectively detect a time period during the night, the subject's sleep, or the subject's lying down position. In another example, the subject, caregiver or other user enters an indication of the subject's night cough into external user interface 104 or 140 of parameter collection device 150. An increase in night coughing (or coughing while lying down) occurrences may correlate to an indication of pulmonary edema. As an example, a persistent night cough may correlate to an indication of pulmonary edema.

In another example, the subject's feeling of anxiety is used as a pulmonary edema related factor 170R. In one example, the subject, caregiver or other user enters an indication of the subject's anxiety level into external user interface 104 or 140 of parameter collection device 150. As an example, the indication of the subject's anxiety level may be based on observations of twitching, trembling, perspiration, dry mouth, or difficulty swallowing. In another example, the anxiety level is measured by an implantable sensor 148, such as a muscle tension sensor. An increase in the level of anxiety may correlate to an indication of pulmonary edema.

In another example, the subject's restlessness, which is also sometimes referred to as "agitation," is used as a pulmonary edema related factor 170S. In one example, the subject, caregiver or other user enters an indication of the subject's restlessness (which may be gained from the subject's vital signs such as increased temperature, increased pulse, or increased blood pressure) into external user interfaces 104 or 140 of parameter collection device 150. Restlessness refers to an unpleasant state of extreme arousal. By itself, restlessness may not have much significance; however, if present along with other pulmonary edema related symptoms (e.g., 170A-R, T-Z), an increase in restlessness may be indicative of pulmonary edema.

In another example, the subject's perspiration level is used as a pulmonary edema related factor 170T. In one example, the subject, caregiver or other user enters an indication of the subject's level of perspiration into external user interfaces 104 or 140 of parameter collection device 150. In most cases, perspiration is perfectly natural, especially as a result of exercise or hot temperatures; however, if perspiration increases for some other reason, it may correlate to an indication of pulmonary edema.

In another example, the subject's pallor is used as a pulmonary edema related factor 170U. In one example, pallor is measured by an external blood test (e.g., complete blood count or blood differential), and an indication (e.g., percentage of oxygen in blood) of pallor found by the blood test is input into parameter collection device 150 by the caregiver or other user at external user interfaces 104 or 140. In another example, the subject, caregiver or other user enters an indication of the subject's pallor into external user interface 104 or 140 of parameter collection device 150. Pallor is characterized by an abnormal loss of normal skin or mucous membrane color which develops suddenly or gradually. Pale-looking skin does not necessarily indicate heart disease. As an example, lack of sunlight or inherited paleness may be the reason for the subject's pallor; however, a change in pallor (e.g., significant change in pallor in a short amount of time) may correlate to an indication of pulmonary edema in some circumstances.

In another example, the subject's nasal flaring is used as a pulmonary edema related factor 170V. In one example, the subject, caregiver or other user enters an indication of the subject's increase in nasal flaring (e.g., increase in frequency, size, or duration) into external user interface 104 or 140 of parameter collection device 150. Nasal flaring refers to enlargement of the opening of the subject's nostrils during breathing. Nasal flaring is often an indication that increased effort is required for breathing. While many causes of nasal flaring are not serious, some can be life-threatening (e.g., thoracic fluid accumulation). An increase in nasal flaring (e.g., increase in frequency, size, or duration of nasal flaring), such as persistent and unexplained nasal flaring, may correlate to an indication of pulmonary edema.

In another example, the subject's decreased level of awareness is used as a pulmonary edema related factor 170W. In one example, the subject, caregiver or other user enters an assessment of the subject's decreased level of awareness into external user interface 104 or 140 of parameter collection device 150. A persistent, decreased level of awareness may correlate to an indication of pulmonary edema.

In another example, the subject's heart rate is used as a pulmonary edema related factor 170X. In one example, heart rate is measured using an implantable sensor 148 (e.g., a cardiac signal sense amplifier coupled to an electrode 107, 108, or 109). In another example, the subject, caregiver or other user enters an indication of the subject's heart rate (e.g., based on an external measurement) into external user interface 104 or 140 of parameter collection device 150. An increase in heart rate (e.g., average resting heart rate) may correlate to an indication of pulmonary edema.

In another example, a thoracic impedance associated with a previous pulmonary edema event is used as a pulmonary edema related factor 170H. The previous thoracic impedance is compared to a present thoracic impedance of the subject. In one example, the previous and present thoracic impedance are represented by previous and present near-DC thoracic impedance values, respectively. In another example, the previous and the present thoracic impedance are represented by previous and present posture-compensated thoracic impedance values, respectively. In another example, the previous and present thoracic impedance are represented by previous and present blood resistivity-compensated thoracic impedance values, respectively. In another example, the previous thoracic impedance is obtained from a medical history (e.g., via electronic medical database 146) of the same subject from which the present thoracic impedance is obtained. In another example, the previous thoracic impedance is obtained from a medical history (e.g., via electronic medical database 146) of at least one different subject from which the present thoracic impedance is obtained. In this example, the present thoracic impedance is measured by a thoracic impedance measurement circuit 124 via electrodes 107, 108, or 109. A similarity in value between the previous thoracic impedance and the present thoracic impedance correlates to an indication of pulmonary edema. As an example, supposing the subject was previously diagnosed with pulmonary edema and at such time had a thoracic impedance of $Z_{Previous}$. If a present thoracic impedance is sensed and found to be less than or substantially equal to $Z_{Previous}$, an indication of pulmonary edema may exist.

In another example, a physiological parameter (e.g., heart sound, respiratory sound, weight, neurohormone level, creatinine level, or heart wall motion) associated with a previous pulmonary edema event is used as a pulmonary edema related factor 170I. The previous physiological parameter is compared to a present physiological parameter of the subject of the same type. In one example, the previous physiological parameter is obtained from a medical history (e.g., via electronic medical database 146) of the same subject from which the present physiological parameter is obtained. In another example, the previous physiological parameter is obtained from a medical history (e.g., via electronic medical database 146) of at least one different subject from which the present physiological parameter is obtained. In another example, the present physiological parameter is externally measured and entered into parameter collection device 150. In another example, the present physiological parameter is measured by an implantable sensor 148. A similarity in value between the previous physiological parameter and the present physiological parameter may correlate to an indication of pulmonary edema. As an example, supposing the subject was previously diagnosed with pulmonary edema and at such time experienced a 2-3 pound daily increase in weight and serum levels of BNP>500 pg/ml. If the subject is presently experiencing similar daily gains in weight and serum levels of BNP>500 pg/ml, an indication of developing pulmonary edema may exist.

In another example, an environmental parameter associated with a previous pulmonary edema event is used as a pulmonary edema related factor 170J. Examples of environmental parameter types include, but are not limited to, parameters related to altitude, barometric pressure, temperature, air quality, pollen count, and humidity. The previous environmental parameter is compared to a present environment parameter relating to the subject of the same type. In one example, the previous environment parameter is obtained from a medical history (e.g., via electronic medical database 146) of the same subject from which the present environmental parameter is obtained. In another example, the previous environmental parameter is obtained from a medical history (e.g., via electronic medical database 146) of at least one different subject from which the present environmental parameter is obtained. In another example, IMD 102 is capable of acquiring environmental data, such as barometric pressure using a pressure sensor 106 and relative temperature changes using a temperature sensor 106 near the subject. A similarity in value between the previous environmental parameter and the present environmental parameter may help explain why the subject is experiencing an indicative pulmonary edema factor (e.g., 170A-Z). As an example, supposing it is known (from medical history records) that the subject experiences a persistent cough, difficulty breathing, and perspiration whenever the surrounding air temperature reaches 90°. If the subject presently begins experiencing a similar persistent cough, difficulty breathing, and perspiration and a temperature sensor 106 detects an air temperature of 95°, such symptoms may not be the result of pulmonary edema but rather due to environmental parameters (e.g., in this case surrounding air temperature). In another example, since such symptoms are not the result of pulmonary edema, no change to the base thoracic impedance threshold or thoracic impedance signal results.

In another example, a compliance parameter associated with a previous pulmonary edema event is used as a pulmonary edema related factor 170K. Examples of compliance parameters include, but are not limited to, parameters related to medication compliance, dietary compliance, or fluid intake compliance. One type of dietary compliance parameter includes a parameter related to sodium or alcohol intake. Medication compliance parameter types include parameters related to drug administration such as drug type, dosage and time. Examples of drug type includes beta-blockers, angiotensin converting enzyme (ACE) inhibitors, diuretics and the like. The previous compliance parameter is compared to a present compliance parameter of the subject of the same type. In one example, the previous compliance parameter is obtained from a medical history (e.g., via electronic medical database 146) of the same subject from which the present compliance parameter is obtained. In another example, the previous compliance parameter is obtained from a medical history (e.g., via electronic medical database 146) of at least one different subject from which the present compliance parameter is obtained. In another example, IMD 102 is capable of acquiring medication compliance by monitoring a measurable parameter correlated to compliance. In another example, blood pressure is monitored to verify that a patient is compliant with hypertensive medications. A similarity in value between the previous compliance parameter and the present compliance parameter may help explain why the subject is experiencing an indicative pulmonary edema factor (e.g., 170A-Z). As an example, supposing it is known (from medical history records 146) that the subject experiences an increase in thoracic impedance of $\Delta Z$ wherever he/she has a sodium intake (e.g., dietary parameter) of >2 g/day. If a similar $\Delta Z$ increase is presently detected within the subject and it is determined (e.g., via information input into parameter collection device 150) that the subject has a daily intake of sodium >2 g, such thoracic impedance increase may not be the result of pulmonary edema but rather due to dietary parameters (e.g., high salt intake). In another example, since such thoracic impedance may not be the result of pulmonary edema, no change to the base thoracic impedance threshold or thoracic impedance signal may result.

In another example, a patient symptom parameter (e.g., shortness of breath, difficulty breathing, wheezing, coughing, feeling of anxiety, feeling of restlessness, perspiration, pallor, nasal flaring, decreased awareness, or increased heart rate) associated with a previous pulmonary edema event is used as a pulmonary edema related factor 170L. The previous patient symptom parameter is compared to a present patient symptom parameter of the subject of the same type. In one example, the previous patient symptom is obtained from a medical history (e.g., via electronic medical database 146) of the same subject from which the present patient symptom is obtained. In another example, the previous patient symptom is obtained from a medical history (e.g., via electronic medical database 146) of at least one different subject. In another example, the present patient symptom parameter is externally measured and entered into parameter collection device 150. In another example, the present patient symptom parameter is measured by an implantable sensor 148. A similarity in frequency, duration, or amplitude between the previous patient symptom parameter and the present patient symptom parameter may correlate to an indication of pulmonary edema.

The above discussed pulmonary edema related factors are not meant to be exhaustive, and may include other physiologic information 170G, other parameters associated with previous pulmonary edema events 170M, or other patient symptoms 170Y not herein discussed.

In a further example, therapy control module 164 adjusts or initiates a therapy provided to the subject using the determined pulmonary edema indication recognized from the comparison between the sensed thoracic impedance signal or variation thereof and the base or adjusted thoracic impedance threshold. As mentioned above, the change to the base thoracic impedance threshold or thoracic impedance signal may depend upon one or more of the pulmonary edema related factors 170A-Z.

The therapy adjusted or initiated by the therapy control module 164 may be selected from a therapy group consisting essentially of: cardiac rhythm management therapy (CRM), dietary therapy, and breathing assistance therapy. In one example, therapy control module 164 adjusts or initiates a cardiac rhythm management therapy provided by a therapy circuit 132 to heart 112 via electrodes 107, 108, or 109. In another example, CRM therapy may include bradycardia pacing therapy, cardioversion/defibrillation therapy, drug therapy, or cardiac resynchronization therapy. Depending on the subject's condition and reason for his/her pulmonary edema, the subject may receive one or more of a variety of medications or a regimen indicating the same. In one example, a diuretic such as furosemide is administered to the subject. Furosemide is a drug that increases the flow of urine that works quickly to expel excess fluid from the subject's body. In another example, morphine is administered to the subject. Caregivers sometimes use morphine to relieve shortness of breath and associated anxiety. In another example, the subject receives afterloaders. Afterloaders dilate the peripheral vessels and take a pressure load off the left ventricle. In a further example, warfarin is administered to the subject. Warfarin is an antithrombotic drug used to reduce the risk of thrombotic events (e.g., stroke, myocardial infraction). If the pulmonary edema is caused by atrial fibrillation warfarin may be indicated. In yet another example, the subject receives blood pressure medications. If the subject has high blood pressure when he/she develops pulmonary edema, as indicated by the pulmonary edema indication, he/she may need medications to control it. On the other hand, if the subject's blood pressure is too low, medications affecting blood pressure may need to be adjusted.

In another example, therapy control module 164 adjusts or initiates dietary therapy provided to the subject. A subject will be given a lifestyle or diet regimen based upon his/her present diet, some common attributes of each regimen include the following. If the subject smokes, the most important thing he/she can do for their heart and lung health is to stop. Continuing to smoke increases the subject's risk of developing lung problems. A heart-healthy diet is encouraged. Fish is one of the cornerstones of a heart-healthy diet, as it contains omega-3 fatty acids, which help improve blood cholesterol levels and prevent blood clots. It is also important for the subject to eat plenty of fruits and vegetables, which contain antioxidants. Antioxidants are vitamins and minerals that help prevent everyday wear and tear on the subject's coronary arteries. The subject should limit his/her intake of all types of fats to no more than 30 percent of his/her daily calories, and saturated and trans fats to 10 percent or less. Further, it is especially important for the subject to limit his/her salt intake, especially if he/she has heart disease. For instance, in some people with impaired left ventricular function, excess salt—even in a single meal—may be enough to trigger congestive heart failure. Further yet, it is important for the subject to incorporate folic acid into his/her diet. Adequate folic acid may reduce blood levels of homocysteine, an amino acid that may be associated with cardiovascular disease.

In a further example, therapy control module 164 adjusts or initiates breathing assistance therapy provided to the subject. Breathing assistance therapy includes, among other things, administering oxygen through a face mask or nasal cannula or the like.

Figure 5:
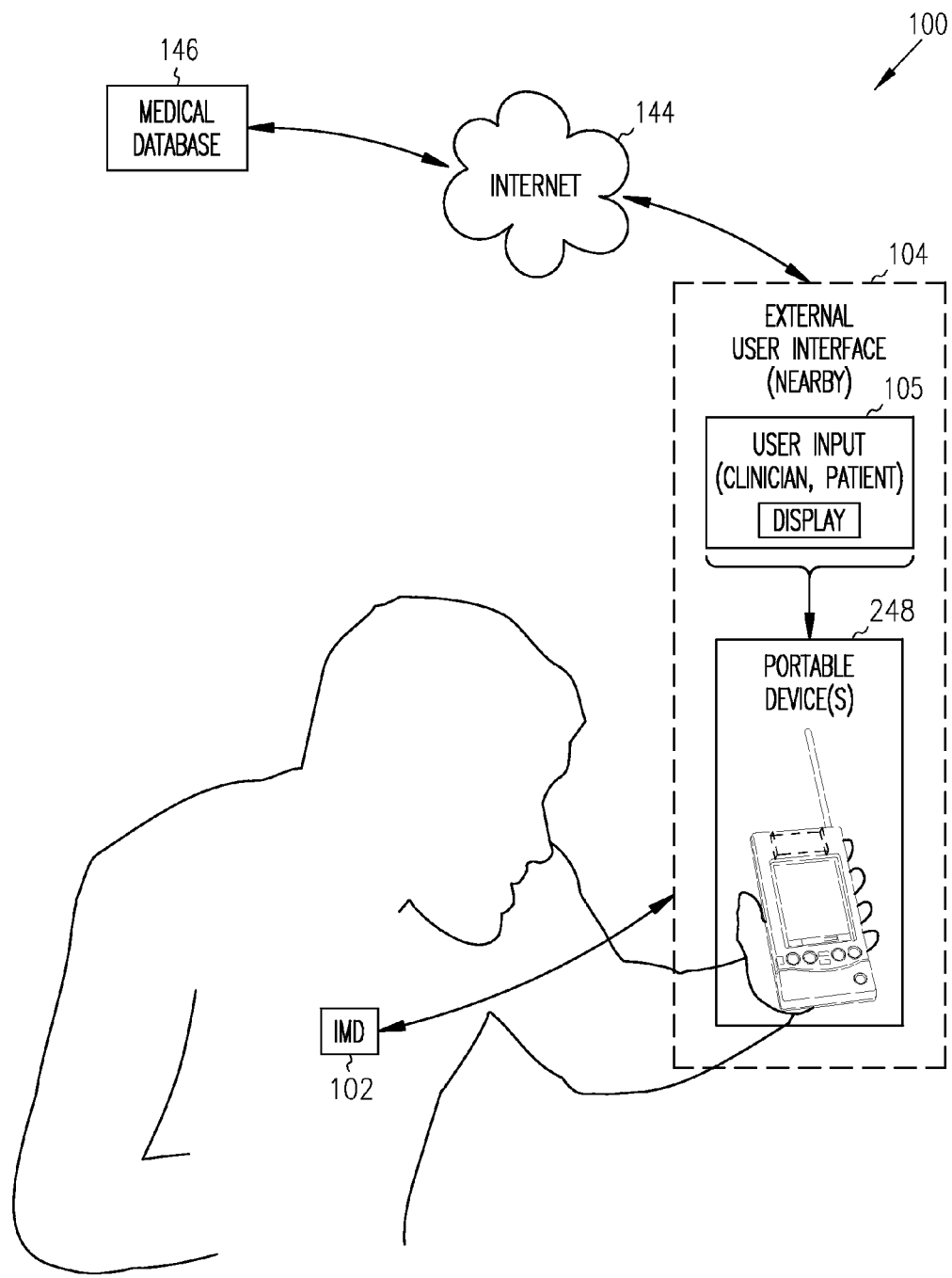
FIG. 5 is a schematic view illustrating portions of a system including an IMD and an external user interface communicatable with an electronic medical database, the system is adapted to enhance the detection of pulmonary edema.

FIG. 5 is a schematic view illustrating portions of a system 100 capable of accurate, enhanced detection of pulmonary edema as a result of, in addition to thoracic impedance measurements, one or a combination of: physiologic information about a subject, at least one statistical parameter regarding a variability of the thoracic impedance measurements, a user-programmable thoracic impedance detection level, at least one parameter associated with a previous pulmonary edema event, and patient symptom information about the subject. In the illustrative example of FIG. 5, system 100 includes an IMD 102, such as a CRM device, and an external user interface 104. As discussed above, in one example, IMD 102 carries various electrical components, such as a communication circuit 138. The communication circuit 138 is capable of wirelessly communicating with a communication circuit of external user interface 104. In another example, communication circuit 138 is capable of wirelessly communicating with a communication circuit of a distant external user interface 140, such as by using a nearby external communication repeater 142. In one example, repeater 142 is coupled to distant user interface 140 by way of an Internet connection 144. In FIG. 5, repeater 142 also communicatively couples IMD 102 to an electronic medical database 146 including the subject's electronic medical records, such as by way of Internet connection 144. Notably, many of the subject's symptoms, lab test results, chart data, etc. from recent and historical physical exams and office visits may be obtained by the present systems, devices, and methods by accessing the subject's electronic medical records via the Internet.

In the example of FIG. 5, external user interface 104 includes a user input device 105 and a display. The user input device 105 provides a means for the subject, caregiver or other user to input data, such as physiologic information about the subject, parameters associated with a pulmonary edema event, a user-programmable thoracic impedance detection level (e.g., threshold), and patient symptom information about the subject, into the external user interface 104 or 140. The display provides a medium to illustrate a graph, histogram or other chart of such data entered by the user or data collected and processed by IMD 102, or to communicate a dietary/lifestyle regimen to the subject. In one example, external user interface 104 is a personal digital assistant (PDA) 248. In another example, distant external user interface 140 is a PDA 248. A PDA is typically a lightweight consumer electronic device that looks like a hand-held computer and can serve as a diary, an alarm, or a personal database.

FIG. 6 is a graph illustrating enhanced (e.g., increased sensitivity of) pulmonary edema detection provided by present systems, devices, and methods. The enhanced detection results in a detection lead-time and thus, alerts a user to the presence of pulmonary edema sooner than a lower sensitivity system, device, or method could provide. As discussed above, as fluid accumulation in the thorax of a subject increases, thoracic impedance decreases. Conversely, as fluid in the thorax depletes, thoracic impedance increases. Typically, a thoracic impedance signal includes cardiac stroke, respiration, posture, or blood resistivity components. Thus, in some examples, the thoracic impedance signal used in comparison to a thoracic impedance threshold is obtained by filtering or compensating the thoracic impedance signal to obtain a near-DC, posture-compensated, or blood resistivity-compensated thoracic impedance signal, respectively. In this example, a near-DC component of the thoracic impedance signal refers to signal frequencies below a cutoff frequency having a value of about 0.05 Hz, such as at signal frequencies between about 0 Hz and about 0.05 Hz, because the cardiac stroke and respiration components of the thoracic impedance signal lie at higher frequencies (e.g., >about 0.05 Hz). In another example, a posture compensation module 136 compensates the thoracic impedance signal using, in part, a posture signal provided by a posture sensor 134. In yet another example, the thoracic impedance signal is adjusted to compensate for changes in blood resistivity. In the illustrative graph of FIG. 6, a near-DC thoracic impedance signal is graphed versus time.

In one example, the system 100 detects the presence of pulmonary edema by comparing the near-DC thoracic impedance signal value to a base thoracic impedance threshold value. If, and when, the near-DC thoracic impedance signal value is less than or substantially equal to the base thoracic impedance threshold value, the subject, caregiver, or other user is alerted of the presence of pulmonary edema. In the graph of FIG. 6, the near-DC thoracic impedance signal (Z)) crosses the base thoracic impedance threshold (Threshold$_{Base}$) at time t$_{Base}$.

The system 100 enhances the detection of pulmonary edema using, in addition to the sensed, filtered, or compensated thoracic impedance, information sensed or received by parameter collection device 150 to adjust the base thoracic impedance threshold, resulting in Threshold$_{Adjusted}$. In one example, information sensed or received by parameter collection device 150 that is indicative of the presence of pulmonary edema results in the adjusted thoracic impedance threshold value being numerically increased from the base thoracic impedance value. In a similar manner, but numerically opposite, information sensed or received by parameter collection device 150 that points away from the presence of pulmonary edema decreases (or leaves unchanged) the thoracic impedance threshold from the base thoracic impedance value. As an example, suppose parameter collection device 150 senses or receives information from the subject including: an increase in heart sound frequency and amplitude, an increase in weight, an increase in BNP and ANP, an increase in creatinine level, and an indication that the regions of the endocardial wall are not moving in a coordinated manner. As discussed above, such information is indicative of pulmonary edema. Accordingly, a numerically increased threshold from Threshold$_{Base}$ to Threshold$_{Adjusted}$ results. In the graph of FIG. 6, the near-DC thoracic impedance signal (Z) crosses a Threshold$_{Adjusted}$ at time t$_{Adjusted}$, resulting in a timely alert to the subject or caregiver. As shown, Threshold$_{Adjusted}$ results in an earlier alert (by Δt) as compared to the alert resulting from Threshold$_{Base}$. Although the foregoing example included the comparison of a near-DC thoracic impedance signal to a base or adjusted thoracic impedance threshold, the present systems, devices, and methods are not so limited. The use of one or a combination of: a sensed thoracic impedance signal, the near-DC thoracic impedance signal, a posture-compensated thoracic impedance signal, and a blood resistivity-compensated thoracic impedance signal is also within the scope of the present systems, devices, and methods.

In another example, system 100 allows for the enhanced detection of pulmonary edema by decreasing the sensed, filtered, or compensated thoracic impedance signal based on the information sensed or received by parameter collection device 150. Typically, such decrease results in the thoracic impedance signal crossing a thoracic impedance threshold at an earlier time. As one such illustrative example, the thoracic impedance signal is multiplied by a factor that is less than 1.0 when factors pointing toward the presence of pulmonary edema are sensed or received.

Figure 7:
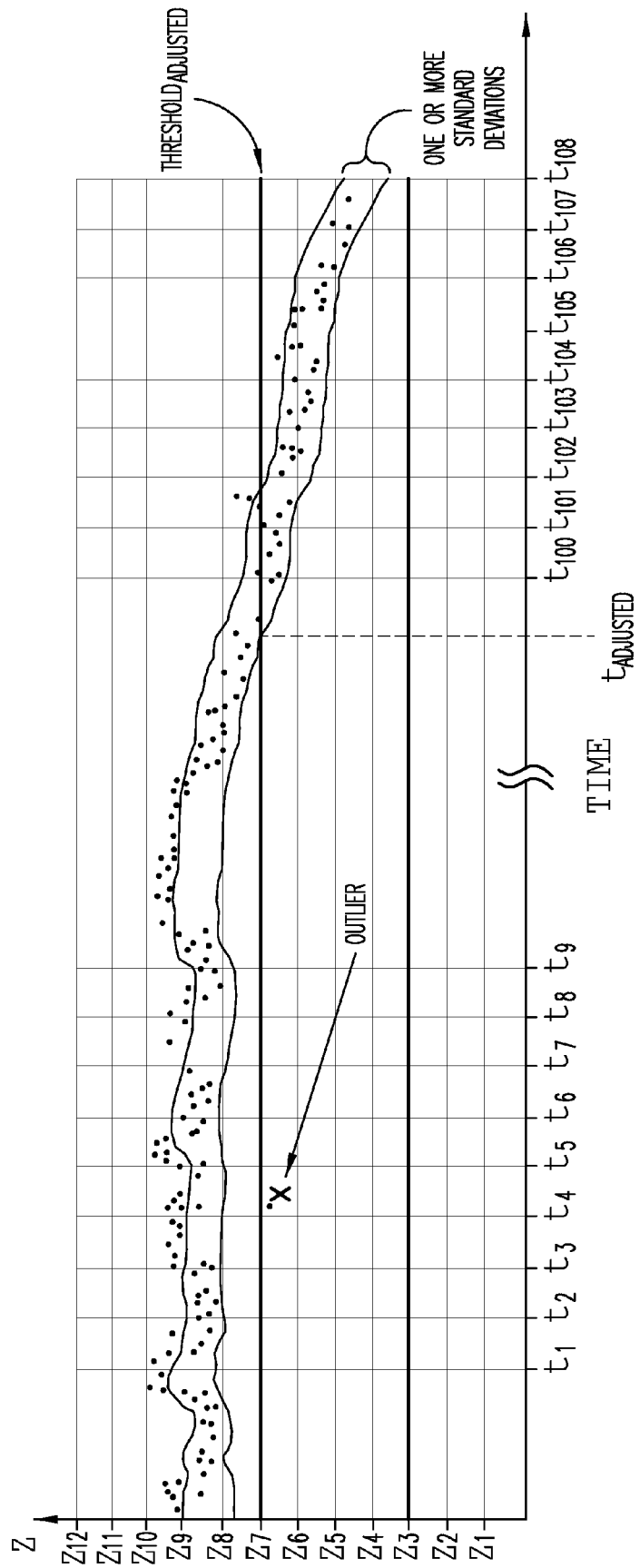
FIG. 7 is a graph illustrating a specificity of a system adapted to enhance the detection of pulmonary edema.

FIG. 7 is a graph illustrating increased specificity of a system capable of enhanced detection of pulmonary edema. As discussed above, an ideal IMD has both 100% sensitivity (e.g., able to effectively detect that which the caregiver desires the IMD to determine or treat) and 100% specificity (able to avoid improperly treating that which the caregiver determines that the device should not treat). In regards to FIG. 6, it was discussed that system 100 is capable of enhanced (e.g., increased sensitivity of) detection of pulmonary edema by using, in addition to thoracic impedance, information sensed or received by parameter collection device 150. The illustrative graph of FIG. 7 illustrates the ability of system 100 to prevent false detections (e.g., increased specificity).

In one example, system 100 increases specificity through the use of at least one statistical parameter regarding the variability of the thoracic impedance signal, such as standard deviation. The at least one statistical parameter may be computed by statistical analysis module 154. Standard deviation is a statistic that indicates how tightly all the various measurements, such as thoracic impedance measurements, are clustered around a mean (e.g., average) in a set of measurements. FIG. 7 illustrates, as an example, the ability of system 100 to discount an "outlier" (a value far from most others in a set of data) when determining and alerting a subject or caregiver to the presence of pulmonary edema. In one example, an "outlier" thoracic impedance measurement is a thoracic impedance that is not within one standard deviation of a mean thoracic impedance. As shown in FIG. 7, a thoracic impedance value (X) less than Threshold$_{Adjusted}$ was measured between the times t$_4$ and t$_5$. Typically, such a measurement would result in the system 100 providing an alert to the subject or caregiver regarding the presence of pulmonary edema. However, system 100 has the capability to characterize X as an outlier since it is not within one standard deviation of the recent mean thoracic impedance (e.g., ten measurement periods) and therefore the system does not issue the alert. Instead, system 100 correctly issues the alert at time t$_{Adjusted}$, the time at which thoracic impedance measurements within one standard deviation of the mean thoracic impedance cross Threshold$_{Adjusted}$. In another example, the at least one statistical parameter may be used by the present systems, devices, and methods in the computation of an adjusted thoracic impedance threshold. In one such example, a high variance of thoracic impedance signals may be indicative that pulmonary edema exists; accordingly, such statistical parameter information is used to compute the adjusted thoracic impedance threshold an increased amount from a base thoracic impedance threshold.

Figure 8:
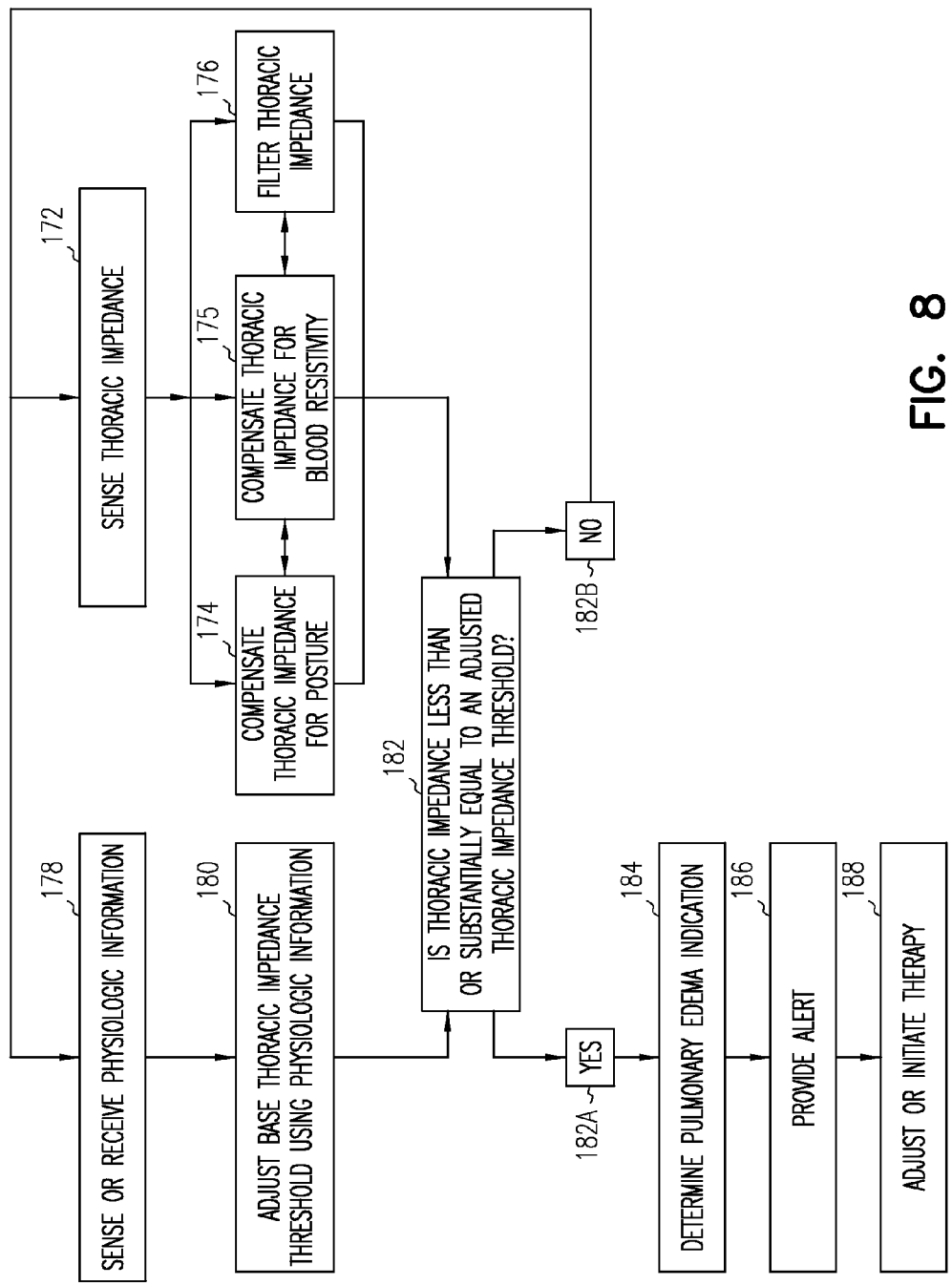
FIG. 8 is a flow chart illustrating one method of enhancing the detection of pulmonary edema.

FIG. 8 is a flow chart illustrating one method of enhancing the detection of pulmonary edema when using thoracic impedance. At 172, a thoracic impedance signal is sensed. This may be accomplished in a number of ways. In one illustrative example, thoracic impedance is measured by delivering a test current between: (1) at least one ring electrode 108 or 109; and (2) a housing electrode 120, and a resulting responsive voltage is measured across a tip electrode 107 and a header electrode 118. In another example, the delivering the test current includes injecting a four-phase carrier signal, such as between the housing electrode 120 and the ring electrode 108. In this example, the first and third phases are +320 microampere pulses that are 20 microseconds long. The second and fourth phases are −320 microampere pulses that are 20 microseconds long. The four phases are repeated at 50 millisecond intervals to provide a test current signal from which a responsive voltage may be measured.

At 174, the sensed thoracic impedance signal or variation thereof (e.g., near-DC thoracic impedance signal or blood resistivity-compensated thoracic impedance signal) is compensated for posture. There are a number of ways in which this can be accomplished. In one example, the system 100 includes a posture sensor 134 and a posture compensation module 136. The posture sensor 134 provides a posture signal indicating a subject's then-current posture. The posture compensation module 136 compensates the sensed thoracic impedance signal using the posture signal. For instance, if a posture signal indicates a subject is in a supine orientation, the posture compensation module 136 may increase the sensed thoracic impedance signal since the supine orientation may have decreased the thoracic impedance signal sensed (indicating an increase in thoracic fluid), as discussed above.

At 175, the sensed thoracic impedance signal or variation thereof (e.g., posture-compensated thoracic impedance signal or near-DC thoracic impedance signal) is compensated for blood resistivity. There are a number of ways in which this can be accomplished. In one example, the blood impedance measurement is performed in the same manner as the thoracic impedance measurement (discussed above), except that measurement of the responsive voltage is across two electrodes that are both typically located in the same chamber of the subject's heart 112 or same blood vessel. Once measured, the controller 126, using the blood impedance measurement, executes a sequence of instructions to compute a blood resistivity correction 137. This blood resistivity correction 137 can then be applied to the sensed thoracic impedance or variation thereof that is received by processor 130. In one example, the sensed thoracic impedance signal is compensated for blood resistivity at 175 before being compensated for posture at 174.

At 176, the sensed thoracic impedance signal or variation thereof (e.g., posture-compensated thoracic impedance signal or blood resistivity-compensated thoracic impedance signal) is filtered. This results in a near-DC thoracic impedance signal. The filtering may be accomplished in a number of ways. In one example, a processor 130 of the system 100 performs any filtering or other signal processing needed to extract from the thoracic impedance signal a near-DC component. In another example, a frequency selective filter circuit 132 performs any filtering or other signal processing needed to extract from the thoracic impedance signal a near-DC component. In another example, filtering is accomplished in a device external to IMD 102. In another example, the sensed thoracic impedance signal is filtered at 176 to obtain a near-DC thoracic impedance signal before being compensated for posture at 174. In yet another example, the sensed thoracic impedance signal is filtered at 176 to obtain a near-DC thoracic impedance signal before being compensated for blood resistivity at 175.

At 178, physiologic information is obtained. There are a number of ways in which such information can be obtained. In one example, system 100 includes a parameter collection device 150 adapted to receive from a user or database or sense (via external or internal sensor) physiologic information from a physiologic information group consisting essentially of: at least one heart sound, at least one lung sound, a respiratory pattern, a weight, a neurohormone level, a creatinine level, and a heart wall motion. In one example, physiologic information is received from the subject, caregiver or other user via external user interface 104. In another example, physiologic information is received from a database via Internet connection 144 and repeater 142. In a further example, physiologic information is externally sensed via external sensor 106. In yet another example, physiologic information is internally sensed via implantable sensor 148 or electrodes 107, 108, or 109.

At 180, a base thoracic impedance threshold is adjusted using the physiologic information sensed or received by parameter collection device 150. In one example, adjusting the base thoracic impedance threshold includes normalizing or weighting the physiologic information received by parameter collection device 150 as discussed above. In another example, system 100 includes a threshold adjustment module 158 that executes instructions to compute a change in the base thoracic impedance threshold based on the physiologic information sensed or received and adjusts the base thoracic impedance threshold using the computed change.

At 182, a comparison between the sensed thoracic impedance signal or variation thereof (e.g., one or a combination of: the near-DC thoracic impedance signal, the posture-compensated thoracic impedance signal, and the blood resistivity-compensated thoracic impedance signal) and an adjusted thoracic impedance threshold is made. In one example, the comparison includes determining whether the near-DC thoracic impedance is less than or substantially equal to the adjusted thoracic impedance threshold. In another example, a pulmonary edema indication is recognized using such comparison. In examples where the near-DC thoracic impedance is not less than, or substantially equal to, the adjusted thoracic impedance threshold, a negative indication of pulmonary edema results at 182(*b*) and the process returns to 172 or 178. In examples where the near-DC thoracic impedance is less than, or substantially equal to, the adjusted thoracic impedance threshold, a positive indication of pulmonary edema results at 182(*a*).

At 184, system 100 determines a positive pulmonary edema indication and provides an alert 186 to the subject or caregiver of the same. The alert may be provided in a number of ways. In one illustrative example, an audible tone is sounded, which prompts the subject to call his/her caregiver. If the subject is linked up to a remote monitoring system (e.g., via repeater 142), the alert can be electronically communicated to the caregiver for review. In another example, the alert is provided (e.g., displayed) to the subject or caregiver at the subject's next visit to his/her caregiver. At 188, a therapy is adjusted or initiated in response to the determined pulmonary edema indication computed. The therapy may be provided in a number of ways. In one example, the therapy is selected from the group consisting essentially of: cardiac rhythm management therapy, dietary therapy, and breathing assistance therapy.

Figure 9:
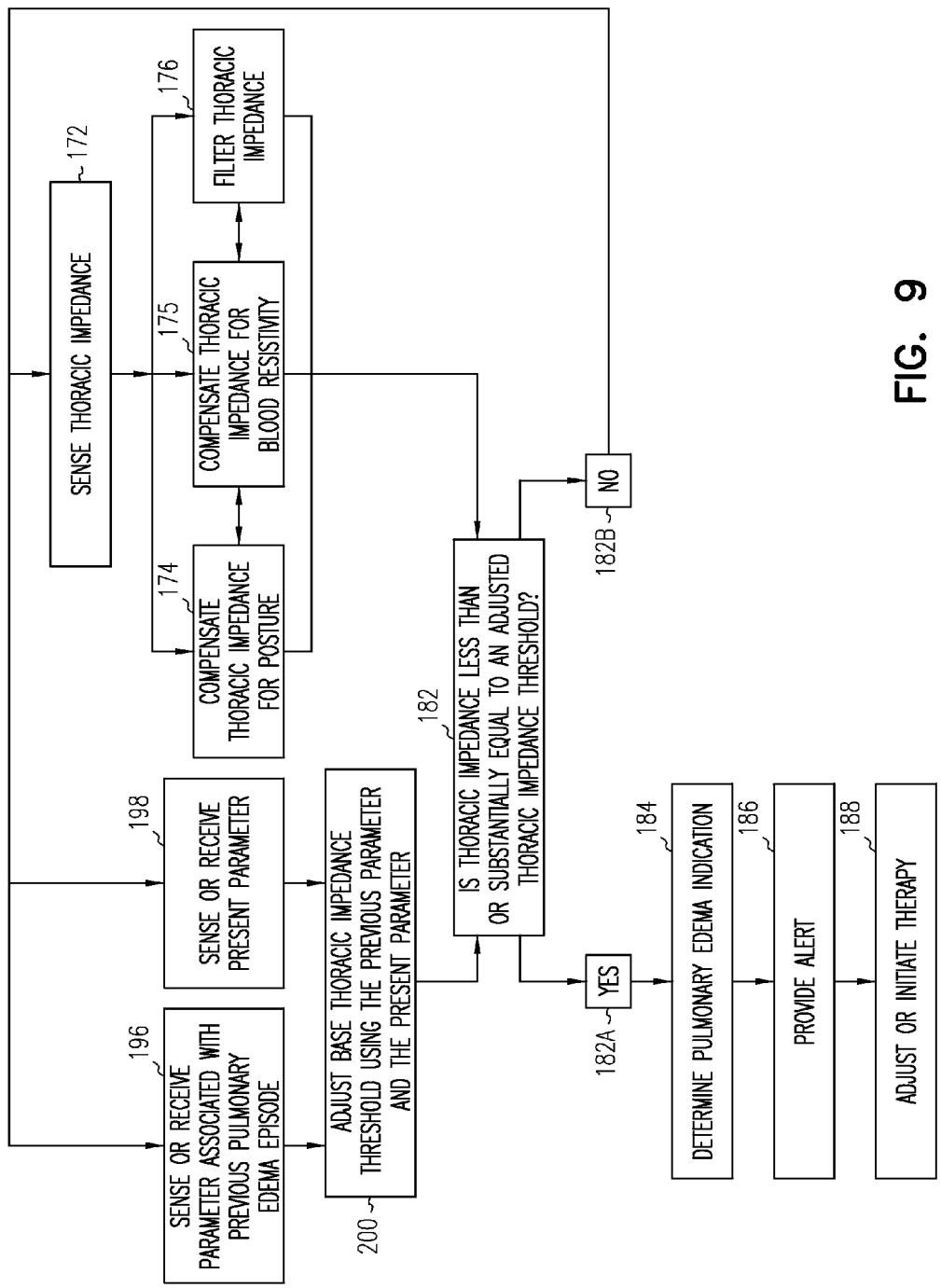
FIG. 9 is a flow chart illustrating another method of enhancing the detection of pulmonary edema.

FIG. 9 is a flow chart illustrating another method of enhancing the detection of pulmonary edema when using thoracic impedance. Method steps 172-188 are similar to the corresponding step numerals of FIG. 8, which are discussed in detail above. However, in the method of FIG. 9, step numerals 196, 198, and 200 replace step numerals 178 and 180 of FIG. 8. Specifically, the method of FIG. 9 increases a sensitivity of pulmonary edema detection using at least one parameter associated with a previous pulmonary edema episode and at least one present parameter of a similar type.

At 196, the at least one parameter associated with a previous pulmonary edema event is sensed or received. This may be accomplished in a number of ways. In one example, system 100 includes a parameter collection device 150 structured to receive from a user or database or sense (via external or internal sensor) the at least one previous parameter associated with a previous pulmonary edema event, which is selected from a previous parameter group consisting essentially of: a previous thoracic impedance, a previous physiologic parameter, a previous environmental parameter, a previous compliance parameter, and a previous patient symptom parameter. In one example, the at least one previous parameter is received from the subject, caregiver or other user via external user interface 104. In another example, the at least one previous parameter is received from a database via Internet connection 144 and repeater 142. In yet another example, the at least one previous parameter is externally sensed via external sensor 106. In a further example, the at least one previous parameter is internally sensed via implantable sensor 148 or electrodes 107, 108, or 109.

At 198, the at least one present parameter is sensed or received. This may be accomplished in a number of ways. In one example, system 100 includes a parameter collection device 150 structured to receive from a user or database or sense (via external or internal sensor) at least one present parameter similar in type to the previous parameter obtained at 196. In one example, the at least one present parameter is received from the subject, caregiver or other user via external user interface 104. In another example, the at least one present parameter is received from a database via Internet connection 144 and repeater 142. In another example, the at least one present parameter is externally sensed via external sensor 106. In another example, the at least one present parameter is internally sensed via implantable sensor 148 or electrodes 107, 108, or 109. In another example, the at least one previous parameter obtained at 196 is from the same subject from which the present parameter is obtained. In yet another example, the at least one previous parameter obtained at 196 is from a different subject from which the present parameter is obtained (e.g., made possible by accessing data in an electronic medical database 146). In a further example, the at least one previous parameter obtained at 196 is from a population of subjects.

At 200, a base thoracic impedance threshold is adjusted using changes to the present parameter obtained at 198 in reference to the previous parameter obtained at 196. In one example, the adjusting the base thoracic impedance threshold includes normalizing or weighting the parameter changes received by parameter collection device 150 as discussed above. In another example, system 100 includes a threshold adjustment module 158 that executes instructions to compute a change in the base thoracic impedance threshold based on the parameter changes received or sensed and adjusts the base thoracic impedance threshold using the computed change.

Figure 10:
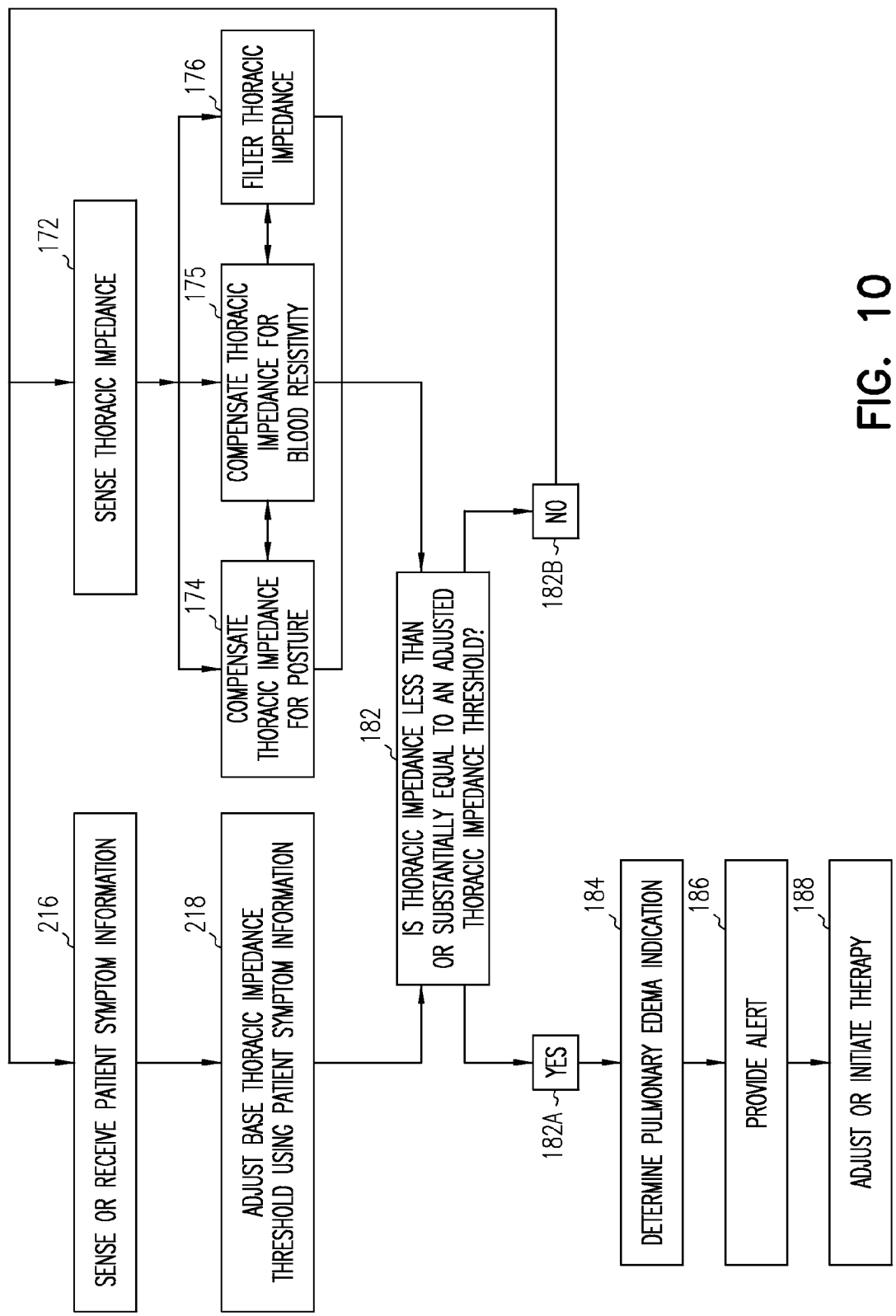
FIG. 10 is a flow chart illustrating a further method of enhancing the detection of pulmonary edema.

FIG. 10 is a flow chart illustrating a further method of enhancing the detection of pulmonary edema when using thoracic impedance. Method steps 172-188 are similar to the corresponding step numerals of FIG. 8, which are discussed in detail above. However, in the method of FIG. 10, step numerals 216 and 218 replace step numerals 178 and 180 of FIG. 8. Specifically, the method of FIG. 10 increases a sensitivity of pulmonary edema detection using patient symptom information about a subject.

At 216, at least one patient symptom from the subject is sensed or received. This may be accomplished in a number of ways. In one example, system 100 includes a parameter collection device 150 adapted to receive from a user or database or sense (via external or internal sensor) the at least one patient symptom, which is selected from a patient symptom group consisting essentially of: a shortness of breath, a difficulty breathing, at least one wheeze, at least one cough, a feeling of anxiety, a feeling of restlessness, an excessive level of perspiration, an indication of pallor, a nasal flare, a decreased level of awareness, and an increased heart rate. In one example, the at least one patient symptom is received from the subject, caregiver or other user via external user interface 104. In another example, the at least one patient symptom is received from a database via Internet connection 144 and repeater 142. In a further example, the at least one patient symptom is externally sensed via external sensor 106. In yet another example, the at least one patient symptom is internally sensed via implantable sensor 148 or electrodes 107, 108, 109.

At 218, a base thoracic impedance threshold is adjusted using the at least one patient symptom sensed or received by parameter collection device 150. In one example, the adjusting the base thoracic impedance threshold includes normalizing or weighting the at least one patient symptom received by parameter collection device 150 as discussed above. In another example, system 100 includes a threshold adjustment module 158 that executes instructions to compute a change in the base thoracic impedance threshold based on the at least one patient symptom sensed or received and adjusts the base thoracic impedance threshold using the computed change.

Heart failure is a common clinical entity, particularly among the elderly, but is often erroneously determined or not determined at the onset using existing systems, devices, and methods. Such erroneous determination or delayed determination may prove fatal in some instances or lead to expensive hospitalization in other instances. As discussed elsewhere in this document, pulmonary edema can be an indicative and important condition associated with heart failure. Advantageously, the present systems, devices, and methods provide sophisticated determination (e.g., detection) and advance warning capabilities regarding the presence of pulmonary edema. By monitoring one or a combination of: physiologic information about the subject, at least one statistical parameter regarding the variability of the thoracic impedance, a user-programmable thoracic impedance detection level, at least one parameter associated with a previous pulmonary edema event, and patient symptom information about the subject, in addition to thoracic impedance, the present systems, devices, and methods accurately enhance the detection of pulmonary edema. Further, the present systems, devices, and methods may accurately enhance the detection of pulmonary edema without requiring the placement of one or more extra leads, and therefore do not provide additional obstacles during implantation.

As discussed above, this Detailed Description is not to be taken in a limiting sense, and the scope of various embodiments is defined only by the appended claims, along with the full range of legal equivalents to which such claims are entitled. In the appended claims, the term "including" (or any variation thereof) is used as the plain-English equivalent of the term "comprising." Also, in the following claims, the terms "including" and "comprising" are open-ended, that is, a system, device, article, or process that includes elements in addition to those listed after such a term in a claim are still deemed to fall within the scope of that claim.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system comprising:
   an implantable thoracic impedance measurement circuit configured to sense a thoracic impedance signal from a subject;
   a parameter collection device configured to sense or receive physiologic information about the subject, the physiologic information including heart wall motion, the parameter collection device including a heart wall dyssynchrony measurement device, wherein the heart wall dyssynchrony measurement device is configured to sense a first heart wall motion signal from a first cardiac site and a second heart wall motion signal from a second cardiac site, and wherein the parameter collection device is configured to provide a heart wall dyssynchrony signal indicative of the heart wall motion from a phase difference between the first heart wall motion signal and the second heart wall motion signal; and
   a pulmonary edema indicator coupled with the thoracic impedance measurement circuit to accept the thoracic impedance signal and coupled with the parameter collection device to accept the heart wall dyssynchrony signal, wherein the pulmonary edema indicator is configured to provide a pulmonary edema indication using the thoracic impedance signal and the heart wall dyssynchrony signal.

2. The system of claim 1, comprising a posture sensor adapted to sense a posture signal, the posture sensor being coupled with the pulmonary edema indicator, wherein the pulmonary edema indicator is configured to provide a pulmonary edema indication using the posture signal.

3. The system of claim 2, comprising a posture compensation module configured to compute a posture-compensated thoracic impedance signal from the thoracic impedance signal using the posture signal, wherein the pulmonary edema indicator is configured to determine the pulmonary edema indication using, at least in part, the posture-compensated thoracic impedance signal.

4. The system of claim 1, wherein:
   the pulmonary edema indicator determines the pulmonary edema indication when the thoracic impedance signal is less than a thoracic impedance threshold; and
   the pulmonary edema indicator includes a threshold adjustment module adapted to adjust the thoracic impedance threshold using, at least in part, the physiologic information driven by the presence or absence of pulmonary edema.

5. The system of claim 1, comprising a frequency selective filter circuit configured to extract from the thoracic impedance signal a near-DC thoracic impedance signal.

6. The system of claim 1, comprising:
   a blood impedance measurement circuit configured to sense a blood impedance signal from the subject; and
   a blood impedance correction module coupled with the blood impedance measurement circuit, wherein the blood impedance correction module is configured to extract from the thoracic impedance signal a blood resistivity-influenced component using the blood impedance signal, and wherein the pulmonary edema indicator is adapted to determine the pulmonary edema indication using, at least in part, a blood resistivity-compensated thoracic impedance signal.

7. The system of claim 1, comprising a therapy control module coupled to the pulmonary edema indicator, wherein the therapy control module is configured to adjust or initiate a therapy based, at least in part, on the pulmonary edema indication, and wherein the therapy includes at least one of: cardiac rhythm management therapy, dietary therapy, and breathing assistance therapy.

8. A method comprising:
   implantably sensing a thoracic impedance signal from the thorax of a subject;
   sensing or receiving physiologic information about the subject, the physiologic information including heart wall motion, wherein sensing or receiving the physiologic information includes:
      sensing a first heart wall motion signal from a first cardiac site and a second heart wall motion signal from a second cardiac site; and
      providing a heart wall dyssynchrony signal indicative of the heart wall motion from a phase difference between the first heart wall motion signal and the second heart wall motion signal; and
   determining, using a processor circuit, a pulmonary edema indication using the thoracic impedance signal and the heart wall dyssynchrony signal, wherein determining the pulmonary edema indication includes comparing the thoracic impedance signal to a thoracic impedance threshold.

9. The method of claim 8, comprising sensing a posture signal corresponding to the posture of the subject, wherein determining, using the processor circuit, the pulmonary edema indication includes using the sensed posture signal.

10. The method as recited in claim 9, comprising one or more of: filtering the thoracic impedance signal to obtain a near-DC thoracic impedance signal, compensating the thoracic impedance signal to attenuate or remove a posture-influenced component of the thoracic impedance signal, and compensating the thoracic impedance signal to attenuate or remove a blood resistivity-influenced component of the thoracic impedance signal,
   wherein determining the pulmonary edema indication includes comparing one or a combination of: the near-DC thoracic impedance signal, a posture-compensated thoracic impedance signal, and a blood resistivity-compensated thoracic impedance signal, to the thoracic impedance threshold.

11. The method as recited in claim 8, comprising:
   increasing the sensitivity of the pulmonary edema indication, including computing a change in the thoracic impedance threshold using the physiologic information;
   adjusting the thoracic impedance threshold using the computed change; and determining the pulmonary edema indication with increased sensitivity using an adjusted thoracic impedance threshold.

12. The method as recited in claim 8, comprising alerting a user in response to the pulmonary edema indication.

13. The method as recited in claim 8, comprising providing a therapy to the subject in response to the pulmonary edema indication, wherein the therapy includes one or a combination of: cardiac rhythm management therapy, dietary therapy, and sleep disordered breathing therapy.

14. A system comprising:
  means for implantably sensing a thoracic impedance signal from the thorax of a subject;
  means for sensing or receiving physiologic information about the subject, the physiologic information including heart wall motion, wherein the means for sensing or receiving the physiologic information includes:
  means for sensing a first heart wall motion signal from a first cardiac site and a second heart wall motion signal from a second cardiac site to provide a heart wall dyssynchrony signal indicative of the heart wall motion from a phase difference between the first heart wall motion signal and the second heart wall motion signal; and
  means for determining a pulmonary edema indication using the thoracic impedance signal and the heart wall dyssynchrony signal, wherein the means for determining the pulmonary edema indication includes means for comparing the thoracic impedance signal to a thoracic impedance threshold.

* * * * *